(12) United States Patent
Anderson et al.

(10) Patent No.: US 8,440,656 B2
(45) Date of Patent: May 14, 2013

(54) METHODS OF TREATING PULMONARY DISEASES AND DISORDERS BY MODULATING CALCIUM/CALMODULIN DEPENDENT PROTEIN KINASE II ACTIVITY

(75) Inventors: Mark E. Anderson, Iowa City, IA (US); Isabella M. Grumbach, Iowa City, IA (US); Joel N. Kline, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 367 days.

(21) Appl. No.: 12/820,802

(22) Filed: Jun. 22, 2010

(65) Prior Publication Data
US 2011/0152172 A1 Jun. 23, 2011

Related U.S. Application Data

(60) Provisional application No. 61/219,245, filed on Jun. 22, 2009.

(51) Int. Cl.
| | | |
|---|---|---|
| A61K 31/54 | (2006.01) | |
| A61K 31/44 | (2006.01) | |
| A61K 31/40 | (2006.01) | |
| A61K 31/19 | (2006.01) | |
| A61K 31/195 | (2006.01) | |

(52) U.S. Cl.
USPC ........ 514/226.5; 514/334; 514/420; 514/557; 514/567

(58) Field of Classification Search ............... 514/226.5, 514/334, 420, 557, 567
See application file for complete search history.

(56) References Cited

U.S. PATENT DOCUMENTS
7,320,959 B2  1/2008  Anderson

OTHER PUBLICATIONS

Aikawa et al., "Marked goblet cell hyperplasia with mucus accumulation in the airways of patients who died of sever acute asthma attack", Chest, 1992, 101:916-921.
Chang et al., "Histone deacetylases 5 and 9 govern responsiveness of the heart to a subset of stress signals and play redundant roles in heart development", Molecular and Cellular Biology, Oct. 2004, 24(19):8467-8476.
Cross, "Inhibitors of the Leukocyte Superoxide Generating Oxidase: Mechanisms of Action and Methods for Their Elucidation", Free Radical Biology & Medicine, 1990, 8:71-93.
Diatchuk et al., "Inhibition of NADPH Oxidase Activation by 4-(2-Aminoethyl)-benzenesulfonyl Fluoride and Related Compounds", Journal of Biological Chemistry, May 16, 1997, 272(20):13292-13301.
Erickson et al., "A dynamic pathway for calcium-independent activation of CaMKII by methionine oxidation", Cell, May 2, 2008, 133(3):462-474.
Horvath et al., "Combined use of exhaled hydrogen peroxide and nitric oxide in monitoring asthma", Am J Respir Crit Car Med, 1998, 158:1042-1046.
Howe et al., "Redox regulation of the calcium/calmodulin-dependent protein kinases", Journal of Biological Chemistry, Oct. 22, 2004, 279(43):44573-44581.
Hudmon et al., "Structure-function of the multifunctional Ca2+/calmodulin-dependent protein kinase II", Biochem J, 2002, 364:593-611.
Jain et al., "Mucosal immunotherapy with CpG oligodeoxynucleotides reverses a murine model of chronic asthma induced by repeated antigen exposure", Am J Physiol Lung Cell Mol Physiol, 2003, 285:L1137-L1146.
Kirkham et al., "Oxidative stress in asthma and COPD: Antioxidants as a therapeutic strategy", Pharmacology & Therapeutics, 2006, 111:476-494.
Levy et al., "Aryl-indolyl maleimides as inhibitors of CaMKII delta. Part 1: SAR of the aryl region", Bioorganic & Medicinal Chemistry Letters, Apr. 1, 2008, 18(7):2390-2394.
Levy et al., "Aryl-indolyl maleimides as inhibitors of CaMKII delta. Part 2: SAR of the amine tether", Bioorganic & Medicinal Chemistry Letters, Apr. 1, 2008, 18(7):2395-2398.
Lu et al., "Aryl-indolyl maleimides as inhibitors of CaMKII delta. Part 3: Importance of the indole orientation", Bioorganic & Medicinal Chemistry Letters, Apr. 1, 2008, 18(7):2399-2403.
Pang et al., "GIT1 Mediates HDAC5 Activation by Angiotensin II in Vascular Smooth Muscle Cells", Arterioscler Thromb Vasc Biol, 2008, 28:892-898.
Pfleiderer et al., "Modulation of vascular smooth muscle cell migration by calcium/calmodulin-dependent protein kinase II-delta2", Am J Physiol Cell Physiol, 2004, 286:C1238-C1245.
Shimura et al., "Continuity of airway goblet cells and intraluminal mucus in the airways of patients with bronchial asthma", Eur Respir J, 1996, 9:1395-1401.
Tanizaki et al., "Mucus Hypersecretion and Eosinophils in Bronchoalveolar Lavage Fluid in Adult Patients with Bronchial Asthma", Journal of Asthma, 1993, 30(4):257-262.
Weiss et al., "Trends in the cost of illness for asthma in the United States, 1985-1994", J Allergy Clin Immunol, 2000, 106:493-499.
Williams et al., "NADPH Oxidase Inhibitors: New Antihypertensive Agents?", J Cardiovasc Pharmacol, Jul. 2007, 50 (1):9-16.
Youn et al., "Calcium Regulates Transcriptional Repression of Myocyte Enhancer Factor 2 by Histone Deacetylase 4", Journal of Biological Chemistry, Jul. 21, 2000, 275(29):22563-22567.
University of Iowa News Release, "'Outsiders' receive grant to study asthma", University of Iowa News Services, Jul. 25, 2008.
University of Iowa Health Care Today, "Heart Research Used to Study Asthma", Aug. 2008.

*Primary Examiner* — Raymond Henley, III
(74) *Attorney, Agent, or Firm* — Andrus, Sceales, Starke & Sawall, LLP

(57) ABSTRACT

Disclosed are methods of treating or preventing a pulmonary disease or disorder in a subject, the methods comprising administering an effective amount of an compound that inhibits Calmodulin Kinase II (CaMKII) activity, either directly or indirectly, thereby treating or preventing the pulmonary disease or disorder in the subject.

13 Claims, 10 Drawing Sheets

METHODS OF TREATING PULMONARY DISEASES AND DISORDERS BY MODULATING CALCIUM/CALMODULIN DEPENDENT PROTEIN KINASE II ACTIVITY

CROSS-REFERENCE TO RELATED APPLICATIONS

The present application claims the benefit of priority to U.S. Provisional Application No. 61/219,245, filed on Jun. 22, 2009, the content of which is incorporated herein by reference in its entirety.

FIELD

The field of the invention relates to methods for treating or preventing pulmonary diseases and disorders by modulating calcium/calmodulin dependent protein kinase II (CaMKII) activity. In particular, the field relates to methods for treating or preventing asthma or the symptoms thereof by inhibiting CaMKII activity

BACKGROUND

Asthma is a disease of airway smooth muscle dysfunction. The prevalence of asthma is between 6-9% of Americans. Asthma leads to significant morbidity and mortality with estimated healthcare and lost opportunity costs of 10.7 billion dollars annually (based on data from 1985-1994) in the United States. (See Weiss et al., 2000). Improved therapies are necessary to reduce suffering and lost productivity in asthma patients. Hypertrophy, hyper-reactivity, pathological remodeling, airway obstruction and inflammation are well established smooth muscle phenotypes in asthma patients, but a unifying biological rationale for these phenotypes was unknown. Present therapies are focused on 'upstream' targets, such as G-protein-coupled receptors (e.g., histamine, adrenergic leukotriene), glucocorticoid receptors and reactive oxygen species that activate signaling pathways important for selective smooth muscle responses in asthma. However, these therapies have not reversed the increase in asthma-related morbidity or mortality. Here it is shown that calmodulin kinase II (CaMKII) is a previously unrecognized, but critical downstream determinant of smooth muscle asthma phenotypes. These findings demonstrate that CaMKII contributes to bronchial hyper-reactivity in vivo and that CaMKII increases mucous accumulation and activates hypertrophic and proinflammatory gene programs in smooth muscle in vitro and in vivo. These findings suggest that CaMKII inhibitors may be utilized in methods for treating asthma and other pulmonary diseases or disorders.

Clinical outcomes in asthma have been linked to increased reactive oxygen species (ROS), airway hyper-reactivity, inflammation and mucous gland hyperplasia, but no previous work has identified a molecular mechanism linking these pro-asthmatic factors. The multifunctional $Ca^{2+}$ and calmodulin dependent protein kinase II (CaMKII) is activated reactive oxygen species (ROS) generated by NADPH oxidase. (See Erickson et al., 2008).

Here, calmodulin kinase II (CaMKII) is shown to be a previously unrecognized, but critical downstream determinant of asthma phenotypes. The results presented here demonstrate that CaMKII contributes to bronchial hyper-reactivity in vivo and that CaMKII is activated by ROS due to NADPH oxidase. Furthermore, activated CaMKII contributes to mucous gland hyperplasia and pulmonary eosinophilia. The results presented here also show that CaMKII inhibition reduces these asthma responses. These findings suggest that CaMKII inhibitors may be utilized in methods for treating asthma and other pulmonary diseases or disorders.

SUMMARY

Calcium/calmodulin dependent protein kinase II (CaMKII) has been found to be associated with pulmonary diseases and disorders such as asthma and asthma-related conditions. Disclosed are methods of treating or preventing a pulmonary disease or disorder in a subject, the methods comprising administering an effective amount of a compound that inhibits Calmodulin Kinase II (CaMKII), thereby treating or preventing the pulmonary disease or disorder in the subject.

The compound administered in the method, i.e., a CaMKII inhibitor, may inhibit one or more isoforms of CaMKII (i.e., one or more of the alpha, beta, delta, and gamma isoforms of CaMKII). Preferably, the compound inhibits at least the delta isoform of CaMKII. The compound may be an aryl-indolyl maleimide compound as disclosed herein. The compound may be KN-93 or an analog or derivative thereof that inhibits CaMKII. Alternatively, the compound may be a peptide.

The CaMKII inhibitor that is administered in the method may inhibit CaMKII directly (e.g., by directly inhibiting the kinase activity of CaMKII) or indirectly (e.g., by inhibiting activation or expression of CaMKII). In some embodiments, the methods include administering to the patient a therapeutic agent that modulates oxidation of CaMKII (e.g., a modulator of NADPH oxidase activity). In further embodiments, the methods may include administering to the patient a therapeutic agent that modulates methionine sulfoxide reductase (Msr) activity or expression in the patient, either directly or indirectly.

The compound may be administered at any suitable dosage. In some embodiments, the compound is administered in a dose of from about 0.05 mg to about 5.0 mg per kilogram of body weight of the subject. In other embodiments, the compound is administered in a dose of from about 0.3 mg to about 3.0 mg per kilogram of body weight of the subject.

The compound may be administered in any suitable pharmaceutical or therapeutic form. In some embodiments, the compound is administered in an inhaled form (e.g., in an aerosolized form delivering between about 5 and about 500 µg inhaled compound per day) or an oral form, which may include a sustained release oral form (e.g., tablets or capsules). In other embodiments, the compound is administered intravenously.

The methods may be utilized to reduce, eliminate, or prevent one or more symptoms associated with a pulmonary disease or disorder such as asthma in a subject. Symptoms treated by the methods may include, but are not limited to, recurrent episodes of shortness of breath (i.e., dyspnea), wheezing, chest tightness, and cough. Suitable subjects for the methods include mammals such as humans.

DETAILED DESCRIPTION

Definitions

Figure 1:
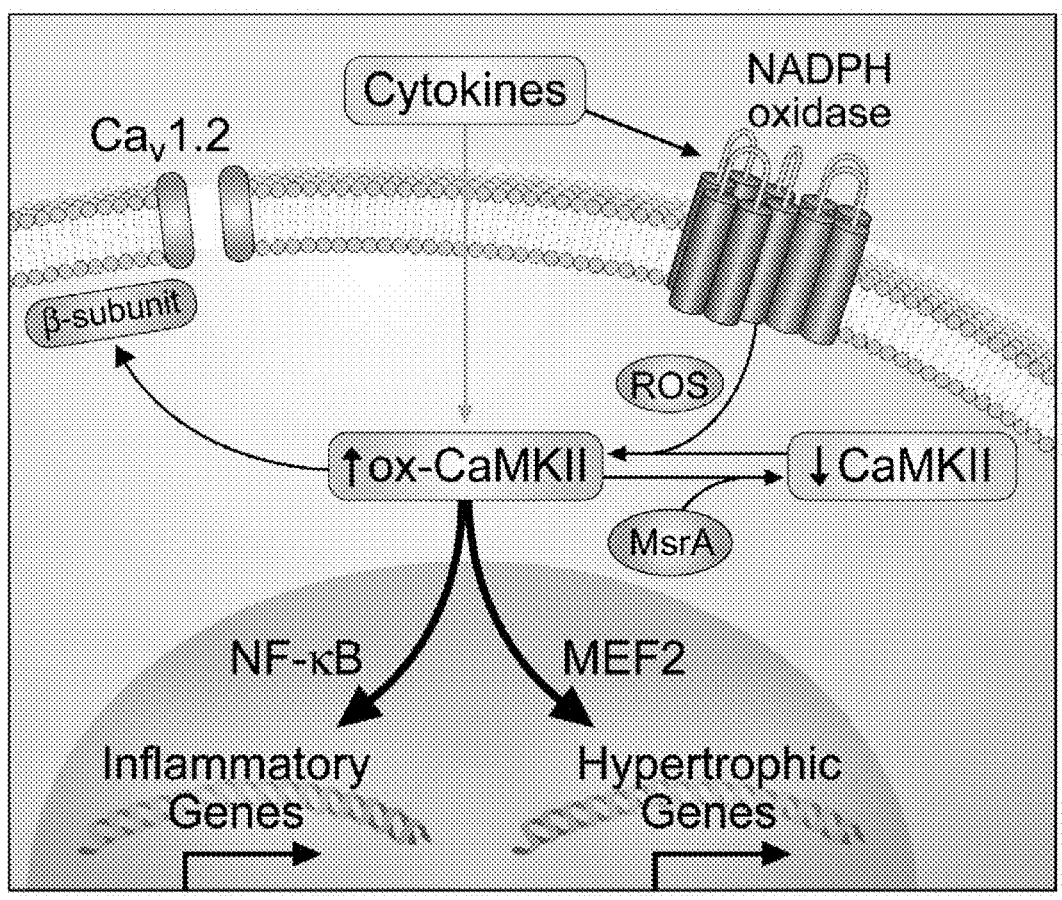
FIG. 1. Role of CaMKII, oxidized CaMKII (ox-CaMKII), reactive oxygen species (ROS), and methionine sulfoxide reductase A (MsrA) in asthma.

The present invention is described herein using several definitions, as set forth below and throughout the application.

As used herein, "a," "an," and "the" mean "one or more" unless the context clearly dictates otherwise. For example, reference to "a CaMKII inhibitor" means one or more CaMKII inhibitors.

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" or "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising."

The presently disclosed methods may be utilized for treating or preventing pulmonary diseases and disorders, such as asthma and asthma-related conditions, and the symptoms thereof. The methods typically comprise administering to a subject in need thereof an effective amount of a compound that modulates the activity of CaMKII (e.g., a CaMKII inhibitor), whereby the administration of the compound treats or prevents the pulmonary diseases and disorders or the symptoms thereof. As used herein, an "effective amount" refers to an amount of a given compound or composition that is necessary or sufficient to bring about a desired biologic effect.

A "patient in need thereof" may include a patient in need of treatment or prevention with respect to a disease or condition associated with calcium/calmodulin dependent protein kinase II. Examples of such diseases or conditions may include, but are not limited to pulmonary diseases or disorders such as asthma and asthma-related conditions. A "patient in need thereof" may include a patient undergoing therapy to treat a pulmonary disease or disorder such as asthma or an asthma-related condition.

As used herein, the terms "treatment," "treat." or "treating" refer to therapy or prophylaxis of pulmonary diseases, disorders, and the symptoms thereof in a subject in need thereof. Therapy or prophylaxis typically results in beneficial or desirable clinical effects, such as alleviation of symptoms, diminishment of extent of disease, stabilization (i.e., not worsening) of the state of the disease, delay or slowing of disease progression, amelioration or palliation of the disease state, and remission (whether partial or total and, whether detectable or undetectable). "Treatment" can also mean prolonging survival as compared to expected survival if a patient were not to receive treatment. Those in need of treatment include those already with the condition or disorder as well as those prone to have the condition or disorder or those in which the condition or disorder is to be prevented.

As used herein, the term "subject" means one in need of treatment or prevention of pulmonary diseases and disorders, such as asthma and asthma-related conditions, or the symptoms thereof. The term "subject" may be used interchangeably herein with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

Pulmonary diseases and disorders treated or prevented by the disclosed methods may include asthma or asthma-related conditions. The term "asthma" is a condition in which the inside of the airways which carry air to the lungs become inflamed, resulting in narrowing of the airways and obstruction to air now. Asthma-related conditions may include, but are not limited to, fibrosis in epithelial organs, acute lung injury, rhinitis, anaphylaxis, sinusitis, hay fever, allergies, vocal cord dysfunction, and gastroesophageal reflux disease. Pulmonary diseases and disorders treated or prevented by the disclosed methods further may include chronic obstructive pulmonary disease (COPD), which may include chronic bronchitis and emphysema. In some embodiments, the presently disclosed methods may be utilized to treat or prevent symptoms of pulmonary diseases or disorders. Symptoms of pulmonary diseases or disorders may include, but are not limited to, recurrent episodes of shortness of breath (i.e., dyspnea), wheezing, chest tightness, and cough.

In some embodiments, the disclosed methods may treat or prevent pulmonary diseases or disorders in a subject via alleviating edema in the lung airways of the subject. In other embodiments, the disclosed methods may treat or prevent pulmonary diseases or disorders in a subject via decreasing mucus production in the lung airways of the subject. In further embodiments, the disclosed methods may treat or prevent pulmonary diseases or disorder in a subject via decreasing epithelial denudation of lung tissue in the subject.

As used herein, "CaMKII" refers to the enzyme "calcium/calmodulin dependent protein kinase II." In humans, there are four separate, highly homologous genes for CaMKII called alpha, beta, delta, or gamma (or $\alpha$, $\beta$, $\delta$ and $\gamma$). Multiple isoforms of these genes are expressed through alternative splicing mechanisms. Representative sequences for the isoforms of these genes have been submitted to public depositories such as GenBank and include: GenBank Accession No. NP_741960. CaMKII alpha isoform 2; GenBank Accession No. NP_057065, CaMKII alpha isoform 1; GenBank Accession No. NP_742079, CaMKII beta isoform 6: GenBank Accession No. NP_742080, CaMKII beta isoform 7: GenBank Accession No. NP_742077. CaMKII beta isoform 4: GenBank Accession No. NP_001211, CaMKII beta isoform 1; GenBank Accession No. NP_742081. CaMKII beta isoform 8: GenBank Accession No. NP_742078. CaMKII beta isoform 5: GenBank Accession No. NP_742076. CaMKII beta isoform 3: GenBank Accession No. NP_742075. CaMKII beta isoform 2; GenBank Accession No. NP_001212, CaMKII delta isoform 3: GenBank Accession No. NP_742126, CaMKII delta isoform 2: GenBank Accession No. NP_742125. CaMKII isoform 1; GenBank Accession No. NP_742113, CaMKII isoform 1; GenBank Accession No. NP_001020609, CaMKII delta isoform 2 (SEQ ID NO:12); NP_751910, CaMKII gamma isoform 3; GenBank Accession No. NP_751913, CaMKII gamma isoform 6: GenBank Accession No. NP_751913. CaMKII gamma isoform 6; GenBank Accession No. NP_751911, CaMKII gamma isoform 1; GenBank Accession No. NP_751909, CaMKII gamma isoform 2; GenBank Accession No. NP_751909, CaMKII gamma isoform 2; GenBank Accession No. NP_001213, CaMKII gamma isoform 4; all of which GenBank entries are incorporated herein by reference in their entireties.

In the disclosed methods, a modulator of CaMKII activity is administered to a subject in need thereof. A modulator of CaMKII activity may include an inhibitor of CaMKII activity. An inhibitor of CaMKII may be any compound, composition, or agent that inhibits, either directly or indirectly, the activity or expression (e.g., the amount or the disease-causing effect) of one or more isoforms of CaMKII (i.e., one or more or the alpha, beta, delta, or gamma isoforms of CaMKII, and preferably at least the delta isoform of CaMKII). For example, a CaMKII inhibitor may be an agent that reduces an activity of CaMKII or that reduces the amount of expression of CaMKII, or both. CaMKII activity in a subject or the amount of CaMKII expression in a subject can be readily determined based on detection or measurement of a functional response. CaMKII inhibition may be reversible or irreversible.

A CaMKII inhibitor that is administered in the method may inhibit CaMKII directly (e.g., by directly inhibiting the kinase activity of CaMKII) or indirectly (e.g., by inhibiting activation of CaMKII). In some embodiments of the methods for treating or preventing pulmonary diseases or disorders in a patient, the methods include administering to the patient a therapeutic agent that inhibits oxidation of CaMKII. For example, the therapeutic agent may inhibit oxidation of CaMKII at methionine residues present at amino acid positions 281 and 282. Agents that inhibit oxidation of CaMKII may include agents that inhibit NADPH oxidase. Inhibitors of NADPH oxidase are known in the art (see Cross, A. R. (1990) Free Rad. Biol. Med. 8, 71-93; and Williams and Griendling, J. Cardiovascular Pharma, July 2007, 50(1):9-16, the contents of which are incorporated by reference in their entireties), and may include, but are not limited to apocynin [4-hydroxy-3-methoxy-acetophenone], diphenylene iodoniumchloride (DPI), staurosporine, phenyl arsine oxide (PAO), 4-(2-Aminoethyl)-benzenesulfonyl fluoride (AEBSF) and related compounds (see Viatchuk, V. et al., J. Biol. Chem. (1997) 272(20):13292-13301, the content of which is incorporated herein by reference in its entirety), gp91ds-tat. PR-39, VAS2870 [3-bezyl-7-(2-benzoxazolyl) thio-1,2,3-triazolo(4,5-d)pyrimidine], and S17834 [6,8-diallyl 5,7-dihydroxy 2-(2-allyl 3-hydroxy 4-methoxyphenyl) 1-H benzo(b)pyran-4-one].

In some embodiments, the disclosed therapeutic methods may include administering to the patient a therapeutic agent that increases methionine sulfoxide reductase (Msr) activity or expression in the patient, either directly or indirectly. The therapeutic agent may increase Msr activity (e.g., by increasing MsrA expression) which subsequently augments the conversion of oxidized methionines in CaMKII to non-oxidized methionines (e.g., augmenting conversion of oxidized methionine residues present at amino acid positions 281 and 282 of CaMKII to non-oxidized states), thereby modulating or inhibiting CaMKII activity.

Inhibitors of CaMKII are known in the art. (See, e.g., U.S. Pat. No. 7,320,959, the content of which is incorporated by reference in its entirety, particular the patent disclosure related to CaMKII inhibitors). A CaMKII inhibitor can be a peptide or non-peptide agent, including, for example, a nucleic acid that encodes a peptide inhibitor. Moreover, the agent can be an antisense nucleic acid that inhibits expression of CaMKII (e.g., in lung tissue). CaMKII inhibitors may include the compound known as KN-93 or related compounds, analogs, or derivatives thereof having CaMKII inhibitory activity. Referring to the PubChem Database provided by the National Center for Biotechnology Information (NCBI) of the National Institute of Health (NIH) at its website, CaMKII inhibitors contemplated herein may include the compounds referenced by compound identification (CID) Nos. 5312122, 16760530, 6419757, which entries are incorporated herein by reference in their entireties. Compounds related to KN-93, analogs, or derivatives thereof may include, for example, compounds referenced by compound identification (CID) Nos. 3837, 6419758, 18412788, 16760530, 9983993, 5353702, 3836, 24906277, 16219540, and 8122359, which entries are incorporated herein by reference in their entireties.

Inhibitors of CaMKII may include aryl-indolyl maleimide compounds. (See. e.g. Levy et al., "Aryl-indolyl maleimides as inhibitors of CaMKIIδ. Part 1: SAR of the aryl region." Biorg. & Medic. Chem. Lett 18 (2008) 2390-2394; Levy et al., "Aryl-indolyl maleimides as inhibitors of CaMKIIδ. Part 2: SAR of the amine tether," Biorg. & Medic. Chem. Lett 18 (2008) 2395-2398; and Lu et al., "Aryl-indolyl maleimides as inhibitors of CaMKIIδ. Part 3: Importance of the indole orientation." Biorg. & Medic. Chem. Lett 18 (2008) 2399-2403: the contents of which are incorporated by reference in their entireties). Suitable aryl-indolyl maleimide compounds for use in the disclosed methods for treating or preventing pulmonary diseases or disorders may include, but are not limited to, the following compounds in Tables 1-14, and analogs and derivatives thereof having CaMKII inhibitory activity (in particular those having CaMKIIδ inhibitory activity):

TABLE 1

| Compound | $R^1$ | $R^2$ | $IC_{50}$ (μM) |
|---|---|---|---|
| $1^9$ | indol-3-yl | $NH_2$ | 0.38 (n = 1) |
| 13a | indol-3-yl | NHBoc | 3.81 ± 0.25 (n = 2) |

TABLE 1-continued

| Compound | $R^1$ | $R^2$ | $IC_{50}$ (μM) |
|---|---|---|---|
| 14b | benzothiophene | $NH_2$ | 0.36 ± 0.01 (n = 2) |
| 13b | benzothiophene | NHBoc | >20 (n = 2) |
| 14c | naphthalen-1-yl | $NH_2$ | 0.29 (n = 1) |
| 14d | naphthalen-2-yl | $NH_2$ | 0.50 ± 0.05 (n = 2) |
| 14e | quinolin-4-yl | $NH_2$ | 0.63 ± 0.04 (n = 2) |
| 14f | quinolin-2-yl | $NH_2$ | >20 (n = 2) |

TABLE 2

| Compound | $R^1$ | $R^2$ | $IC_{50}$ (μM) |
|---|---|---|---|
| $1^9$ | indol-3-yl | $NH_2$ | 0.38 (n = 1) |
| 13a | indol-3-yl | NHBoc | 3.81 ± 0.25 (n = 2) |

TABLE 2-continued

[Structure: indole-maleimide with R¹ substituent and N-propyl-R² chain]

| Compound | R¹ | R² | IC$_{50}$ (μM) |
|---|---|---|---|
| 14g | phenyl | NH$_2$ | 1.35 ± 0.64 (n = 2) |
| 13g | phenyl | NHBoc | >20 (n = 2) |
| 14h | 2-pyridyl | NH$_2$ | 1.58 (n = 1) |
| 14i | 3-pyridyl | NH$_2$ | 0.54 (n = 1) |
| 14j | 4-pyridyl | NH$_2$ | 1.60 (n = 1) |
| 14k | 2-furyl | NH$_2$ | 1.49 ± 0.47 (n = 2) |
| 14l | 2-thienyl | NH$_2$ | 1.19 (n = 1) |
| 13l | 2-thienyl | NHBoc | >20 (n = 1) |

TABLE 3

[Structure: indole-maleimide with R substituent and N-(3-aminopropyl) chain]

| Compound | R | IC$_{50}$ (μM) |
|---|---|---|
| 1[9] | 1H-indol-3-yl | 0.38 (n = 1) |

TABLE 3-continued

[Structure: indole-maleimide with R substituent and N-(3-aminopropyl) chain]

| Compound | R | IC$_{50}$ (μM) |
|---|---|---|
| 14i | 3-pyridyl | 0.54 (n = 1) |
| 14m | 3-bromophenyl | 0.18 ± 0.06 (n = 3) |
| 14n | 3-methylphenyl | 0.28 ± 0.07 (n = 2) |
| 14o | 3-biphenyl | 1.32 ± 0.76 (n = 2) |
| 14p | 3-phenoxyphenyl | 1.68 (n = 1) |

TABLE 4

[Structure: indole-maleimide with R¹ substituent and N-propyl-R² chain]

| Compound | R¹ | R² | IC$_{50}$ (μM) |
|---|---|---|---|
| 1[9] | 1H-indol-3-yl | NH$_2$ | 0.38 (n = 1) |
| 13a | 1H-indol-3-yl | NHBoc | 3.81 ± 0.25 (n = 2) |

TABLE 4-continued

[Structure: bisindolylmaleimide with N-propyl-R² substituent on indole]

| Compound | R¹ | R² | IC₅₀ (μM) |
|---|---|---|---|
| 14q | indol-1-yl | NH$_2$ | 4.56 (n = 1) |
| 14r[12] | 1-methylindol-3-yl | NH$_2$ | 0.31 (n = 1) |
| 14s | 2-methylindol-3-yl | NH$_2$ | 0.75 ± 0.31 (n = 2) |
| 13s | 2-methylindol-3-yl | NHBoc | 7.61 (n = 1) |
| 14t | 5-bromoindol-3-yl | NH$_2$ | 0.034 ± 0.009 (n = 3) |
| 13t | 5-bromoindol-3-yl | NHBoc | 7.54 (n = 1) |

TABLE 5

[Structure: maleimide with indole N-(3-aminopropyl) and N-R² on maleimide]

| Compound | R¹ | R² | IC₅₀ (μM) |
|---|---|---|---|
| 1[9] | indol-3-yl | H | 0.38 (n = 1) |
| 13a | indol-3-yl | CH$_3$ | 3.81 ± 0.25 (n = 2) |
| 14b | benzothiophen-3-yl | H | 0.36 ± 0.01 (n = 2) |
| 16b | benzothiophen-3-yl | CH$_3$ | 2.32 (n = 1) |

TABLE 5-continued

| Compound | R¹ | R² | IC₅₀ (μM) |
|---|---|---|---|
| 14g | phenyl | H | 1.35 ± 0.64 (n = 2) |
| 16g | phenyl | CH$_3$ | 15.02 (n = 1) |
| 14t | 5-bromoindol-3-yl | H | 0.034 ± 0.01 (n = 3) |
| 16t | 5-bromoindol-3-yl | CH$_3$ | >20 (n = 1) |

TABLE 6

[Structure: maleimide with 3-indolyl and R²-substituted N-indole]

| Compound | R¹ | R² | IC₅₀ (μM) |
|---|---|---|---|
| 7a[13] | indol-3-yl | CH$_2$CH$_2$CH$_2$NH$_2$ | 0.38 (n = 1) |
| 7g[13] | indol-3-yl | H | 1.19 (n = 1) |
| 7b | 5-bromoindol-3-yl | CH$_2$CH$_2$CH$_2$NH$_2$ | 0.034 ± 0.009 (n = 3) |
| 7e | 5-bromoindol-3-yl | CH$_3$ | 0.87 (n = 1) |
| 7c | phenyl | CH$_2$CH$_2$CH$_2$NH$_2$ | 1.35 ± 0.64 (n = 2) |
| 7f | phenyl | CH$_3$ | >20 (n = 1) |
| 7h | phenyl | H | >20 (n = 1) |
| 7d | 3-bromophenyl | CH$_2$CH$_2$CH$_2$NH$_2$ | 0.18 ± 0.06 (n = 3) |
| 7i | 3-bromophenyl | H | 3.53 (n = 1) |

TABLE 7

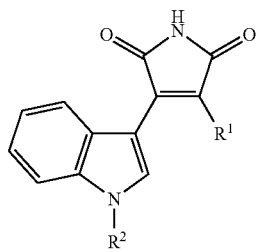

| Compound | R[1] | R[2] | IC$_{50}$ (μM) |
|---|---|---|---|
| 7a[13] | 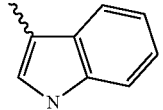 (indol-3-yl) | CH$_2$CH$_2$CH$_2$NH$_2$ | 0.38 (n = 1) |
| 6a |  | CH$_2$CH$_2$CH$_2$NHBoc | 3.81 ± 0.25 (n = 2) |
| 7b | 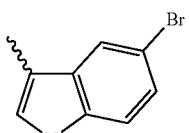 (5-Br-indol-3-yl) | CH$_2$CH$_2$CH$_2$NH$_2$ | 0.034 ± 0.009 (n = 3) |
| 6b |  | CH$_2$CH$_2$CH$_2$NHBoc | 7.54 (n = 1) |
| 7c | 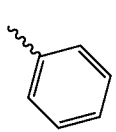 (phenyl) | CH$_2$CH$_2$CH$_2$NH$_2$ | 1.35 ± 0.64 (n = 2) |
| 6c |  | CH$_2$CH$_2$CH$_2$NHBoc | >20 (1 = 2) |

TABLE 8

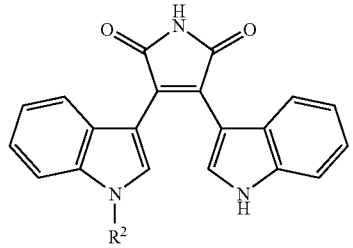

| Compound | R | IC$_{50}$ (μM) |
|---|---|---|
| 7a[13] | 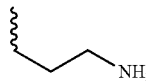 CH$_2$CH$_2$CH$_2$NH$_2$ | 0.38 (n = 1) |
| 7j[14] | 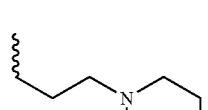 (butyl-piperazine) | 2.02 (n = 1) |
| 7k[14] | 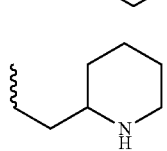 (2-piperidinyl-ethyl) | 1.45 (n = 1) |

TABLE 8-continued

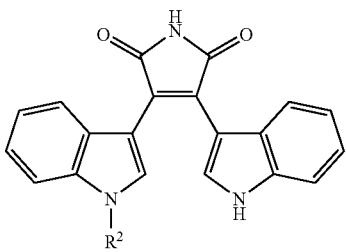

| Compound | R | IC$_{50}$ (μM) |
|---|---|---|
| 7l[13] |  (N-methylpyrrolidinyl-ethyl) | 1.89 (n = 1) |

TABLE 9

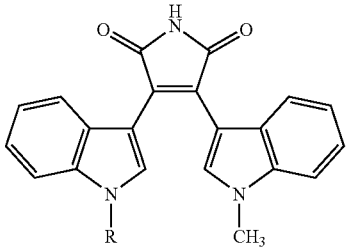

| Compound | R | IC$_{50}$ (μM) |
|---|---|---|
| 7m[13] |  CH$_2$CH$_2$CH$_2$NH$_2$ | 0.31 (n = 1) |
| 7n |  (piperidin-3-yl) | 0.30 (n = 1) |
| 7o |  (piperidin-4-yl) | 0.64 (n = 1) |
| 7p | 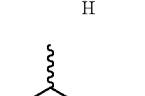 (1-benzylpiperidin-4-yl) | 1.87 ± 0.18 (n = 2) |

TABLE 10

| Compound | R | IC$_{50}$ (μM) |
|---|---|---|
| 7c | –CH$_2$CH$_2$CH$_2$NH$_2$ | 1.35 ± 0.64 (n = 2) |
| 7q | –CH$_2$CH(OH)CH$_2$NH$_2$ | 0.45 (n = 1) |

TABLE 11

| Compound | R$^1$ | IC$_{50}$ (μM) fresh | IC$_{50}$ (μM) old |
|---|---|---|---|
| 2 | benzothiophen-3-yl | 0.36 ± 0.01 (n = 2) | <0.039 |
| 3 | phenyl | 1.35 ± 0.64 (n = 2) | 0.23 |

TABLE 12

| Compound | X | Y | IC$_{50}$ (μM) |
|---|---|---|---|
| 14 | indol-3-yl (N-linked via propylamine) | 1H-indol-3-yl | 0.38 (n = 1) |
| 15 | indol-3-yl (N-linked via propylamine) | 2-methyl-1H-indol-3-yl | 0.75 ± 0.31 (n = 2) |
| 16 | indol-3-yl (N-linked via propylamine) | 1H-indol-1-yl | 4.56 (n = 1) |
| 17 | 2-methyl-indol-3-yl (N-linked via propylamine) | 1H-indol-3-yl | 0.74 (n = 1) |
| 18 | indol-1-yl | 1H-indol-3-yl | 0.19 ± 0.01 (n = 2) |
| 19 | indazol-3-yl (N1-linked) | 1H-indol-3-yl | 0.38 ± 0.06 (n = 2) |

TABLE 13

| Compound | R | IC$_{50}$ (μM) |
|---|---|---|
| 18 | -CH$_2$CH$_2$CH$_2$NH$_2$ | 0.19 ± 0.01 (n = 2) |
| 20 | -CH$_2$CH$_2$CH$_2$N(CH$_3$)$_2$ | 0.74 (n = 1) |
| 21 | -CH$_2$CH$_2$CH$_2$OH | 6.00 (n = 1) |
| 22 | -CH$_2$CH$_2$NH$_2$ | 0.11 ± 0.05 (n = 2) |
| 23 | -CH$_2$CH$_2$NHCH$_3$ | 0.15 (n = 1) |
| 24 | -CH$_2$CH$_2$N(CH$_3$)$_2$ | 0.56 ± 0.10 (n = 2) |
| 25 | -CH$_2$N(CH$_3$)$_2$ | 2.41 ± 0.20 (n = 2) |
| 26 | 4-piperidinyl | 0.68 ± 0.003 (n = 2) |

TABLE 14

| Compound | R$^1$ | R$^2$ | IC$_{50}$ (μM) |
|---|---|---|---|
| 22 | H | H | 0.11 ± 0.05 (n = 2) |
| 23 | CH$_3$ | H | 0.15 (n = 1) |
| 27 | H | Cl | 0.010 (n = 1) |
| 28 | CH$_3$ | Cl | 0.013 (n = 1) |
| 29 | H | F | 0.038 ± 0.008 (n = 2) |
| 30 | H | CF$_3$ | 0.032 (n = 1) |
| 31 | H | CN | 0.046 ± 0.004 (n = 2) |
| 32 | CH$_3$ | CH$_2$CH$_3$ | 0.11 ± 0.03 (n = 3) |
| 33 | H | OCH$_3$ | 0.17 ± 0.06 (n = 2) |
| 34 | CH$_3$ | CO$_2$CH$_3$ | 0.021 ± 0.003 (n = 2) |
| 35 | CH$_3$ | CO$_2$H | 0.38 ± 0.10 (n = 2) |
| 36 | CH$_3$ | CONH$_2$ | 0.19 (n = 1) |
| 37 | CH$_3$ | CONHCH$_3$ | 0.28 (n = 1) |
| 38 | CH$_3$ | CON(CH$_3$)$_2$ | 11.85 (n = 1) |

Methods of measuring CaMKII activity and identifying CaMKII inhibitors are known in the art. (See, e.g., U.S. Pat. No. 7,320,959; Levy et al., "Aryl-indolyl maleimides as inhibitors of CaMKIIδ. Part 1: SAR of the aryl region," Biorg. & Medic. Chem. Lett 18 (2008) 2390-2394; Levy et al., "Aryl-indolyl maleimides as inhibitors of CaMKIIδ. Part 2: SAR of the amine tether," Biorg. & Medic. Chem. Lett 18 (2008) 2395-2398; and Lu et al. "Aryl-indolyl maleimides as inhibitors of CaMKIIδ. Part 3: Importance of the indole orientation." Biorg. & Medic. Chem. Lett 18 (2008) 2399-2403: the contents of which are incorporated by reference in their entireties).

In the presently disclosed therapeutic methods, a CaMKII inhibitor may be administered as part of a pharmaceutical composition. The term "pharmaceutical composition" may be utilized herein interchangeably with the term "therapeutic formulation." Therapeutic formulations of the CaMKII inhibitors used in accordance with the present methods may be prepared for storage by mixing the CaMKII inhibitor having a desired degree of purity with optional pharmaceutically acceptable carriers, excipients or stabilizers (Remington's Pharmaceutical Sciences 16th edition, Osol, A. Ed. (1980)), for example in the form of lyophilized formulations or aqueous solutions. In addition to the pharmacologically active compounds such as the CaMKII inhibitor, the compositions used in the therapeutic methods disclosed herein may contain one or more suitable pharmaceutically acceptable carriers comprising excipients and auxiliaries that facilitate processing of the active compounds into preparations that can be used pharmaceutically.

In the present methods, CaMKII inhibitors may be administered together with a pharmaceutically acceptable carrier. A "pharmaceutically acceptable" carrier typically is not biologically or otherwise undesirable, i.e., the carrier may be administered to a subject, along with the CaMKII inhibitor without causing any undesirable biological effects or interacting in a deleterious manner with the CaMKII inhibitor or any of the other components of the pharmaceutical composition in which the CaMKII inhibitor is contained. In some embodiments, the carrier may be selected to minimize any degradation of the CaMKII inhibitor or any of the other components of the pharmaceutical composition or to minimize any adverse side effects in the subject.

In the present methods, the CaMKII inhibitor may be administered in any suitable manner. In some embodiments, the CaMKII inhibitor is present in a pharmaceutical composition that is administered orally, parenterally (e.g., intravenously, intramuscularly, intrathecally, or intraarterially), transdermally, extracorporeally, topically, intranasally, or via an inhalant. As used herein, "intranasal" administration may include delivery of a pharmaceutical composition into the nose and nasal passages through one or both of the nares and may include delivery via a spraying mechanism or droplet mechanism, or via aerosolization of the therapeutic agent. The pharmaceutical composition may be delivered to the lower respiratory tract (e.g., trachea, bronchi and lungs) via intubation.

For aerosol administration, CaMKII inhibitors may be supplied in finely divided form along with a surfactant and propellant. Typical percentages of CaMKII inhibitors in aerosol formulation may be 0.01%-20% by weight, preferably 1-10%. The surfactant is non-toxic and preferably is soluble in the propellant. Surfactants may include esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. The surfactant may constitute 0.1%-20% by weight of the composition, preferably 0.25-5%. The balance of the composition is ordinarily propellant. A carrier can also be included, as desired, as with, e.g., lecithin for intranasal delivery.

The pharmaceutical preparations utilized in the methods disclosed herein may be manufactured by means that include, but are not limited to, mixing, granulating, dragee-making, dissolving, or lyophilizing processes. Thus, for example, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients for the pharmaceutical compositions utilized in the disclosed methods may include, but are not limited to, fillers such as saccharides (e.g. lactose or sucrose, mannitol or sorbitol), cellulose preparations and/or calcium phosphates (e.g., tricalcium phosphate or calcium hydrogen phosphate), as well as binders (e.g., starch paste, using, for example, maize starch, wheat starch, rice starch, potato starch, gelatin, tragacanth, methyl cellulose, hydroxypropylmethylcellulose, sodium carboxy-methylcellulose, or polyvinyl pyrrolidone).

The pharmaceutical compositions or therapeutic formulation utilized in the methods disclosed herein may include disintegrating agents, such as maize starch, wheat starch, rice starch, potato starch, carboxymethyl-starch, cross-linked polyvinyl pyrrolidone, agar, or alginic acid or a salt thereof, such as sodium alginate. The pharmaceutical compositions or therapeutic formulation further may include auxiliaries as flow-regulating agents or lubricants, for example silica, talc, stearic acid or salts thereof, such as magnesium stearate or calcium stearate, and/or polyethylene glycol. The pharmaceutical compositions or therapeutic formulations may include coated tablets or dragee cores. For example, coatings may comprise concentrated saccharide solutions, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, may be used.

Other pharmaceutical preparations that can be used orally in the methods disclosed herein include push-fit capsules made of gelatin, as well as soft, sealed capsules made of gelatin and a plasticizer such as glycerol or sorbitol. The push-fit capsules may contain the CaMKII inhibitor in the form of granules that may be mixed with fillers such as lactose, binders such as starches, and/or lubricants such as talc or magnesium stearate and, optionally, stabilizers. In soft capsules, the CaMKII inhibitor may be dissolved or suspended in suitable liquids such as fatty oils or liquid paraffin. In addition, stabilizers may be added.

Suitable formulations for parenteral administration in the methods disclosed herein include aqueous solutions of the CaMKII inhibitor in water-soluble form, for example water-soluble salts and alkaline solutions. Aqueous injection suspensions can contain substances that increase the viscosity of the suspension, for example sodium carboxymethyl cellulose, sorbitol, and/or dextran. Optionally, the suspension may also contain stabilizers.

Sustained-release preparations of a CaMKII inhibitor for use in the present methods may be prepared as known in the art. Suitable examples of sustained-release preparations include semipermeable matrices of solid hydrophobic polymers containing the CaMKII inhibitor, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, non-degradable ethylene-vinyl acetate, and poly-D-(−)-3-hydroxybutyric acid.

Formulations to be used for in vivo administration in the disclosed methods typically are sterile. Sterile compositions may be prepared, for example, by filtration through sterile filtration membranes.

The exact amount of the compositions delivered in the disclosed methods may vary from subject to subject, depending on the species, age, weight and general condition of the subject, the severity of the condition being treated, the particular composition used (e.g., with respect to concentration of CaMKII inhibitor in the composition), its mode of administration, and the like. In some embodiments, a CaMKII inhibitor is administered in a dose that is effective to inhibit CaMKII activity in the subject at the site at which the CaMKII inhibitor is delivered. More specifically, a CaMKII inhibitor may be administered in a dose of from about 0.05 mg to about 5.0 mg per kilogram of body weight of the subject. A CaMKII inhibitor, alternatively, may be administered in a dose of from about 0.3 mg to about 3.0 mg per kilogram of body weight of the subject.

In some embodiments of the disclosed methods, a CaMKII inhibitor may be administered to the patient (e.g., as an aerosol) in a dosage of between about 1 mg/ml and about 500 mg/ml. For example, a CaMKII inhibitor may be administered in a dosage of about 1 mg/ml, 2 mg/ml, 3 mg/ml, 4 mg/ml, 5 mg/ml, 10 mg/ml, 15 mg/ml, 20 mg/ml, 25 mg/ml, 30 mg/ml, 35 mg/ml, 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml, 100 mg/ml, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml, 165 mg/ml, 170 mg/ml, 175 mg/ml, 180 mg/ml, 185 mg/ml, 190 mg/ml, 195 mg/ml, 200 mg/ml, 205 mg/ml, 210 mg/ml, 215 mg/ml, 220 mg/ml, 225 mg/ml, 230 mg/ml, 235 mg/ml, 240 mg/ml, 245 mg/ml, 250 mg/ml, 255 mg/ml, 260 mg/ml, 265 mg/ml, 270 mg/ml, 275 mg/ml, 280 mg/ml, 285 mg/ml, 290 mg/ml, 295 mg/ml, 300 mg/ml, 305 mg/ml, 310 mg/ml. 315 mg/ml, 320 mg/ml. 325 mg/ml, 330 mg/ml, 335 mg/ml, 340 mg/ml, 345 mg/ml. 350 mg/ml, 355 mg/ml. 360 mg/ml. 365 mg/ml, 370 mg/ml, 375 mg/ml, 380 mg/ml. 385 mg/ml, 390 mg/ml, 395 mg/ml or 400 mg/ml.

In the methods, a CaMKII inhibitor may be administered according to a wide variety of dosing schedules. For example, a CaMKII inhibitor may be administered once daily for a predetermined amount of time (e.g., four to eight weeks, or more), or according to a weekly schedule (e.g., one day per week, two days per-week, three days per week, four days per week, five days per week, six days per week or seven days per week) for a predetermined amount of time (e.g., four to eight weeks, or more).

The present methods for treating pulmonary conditions or disorders (e.g., asthma or symptoms thereof) may include administering to a patient a first agent in conjunction with a second agent, wherein the first agent is a CaMKII inhibitor and the second agent is an agent that is useful for treating pulmonary conditions or disorders (e.g., asthma or symptoms thereof) but which second agent is not necessarily a CaMKII inhibitor. By administering a first agent "in conjunction with" a second agent is meant that the first agent can be administered to the patient prior to, simultaneously with, or after, administering the second agent to the patient, such that both agents are administered to the patient during the therapeutic regimen. For example, according to some embodiments of the present method, a CaMKII inhibitor is administered to a patient in conjunction (i.e., before, simultaneously with, or after) administration of a second agent for treating asthma, asthma-related conditions, or symptoms thereof.

In some embodiments, the methods disclosed herein may be used to treat a mammal having or at risk of having a pulmonary disease or disorder (e.g. asthma), comprising co-administering to the mammal a therapeutically effective dose of a CaMKII inhibitor and one or more additional active agents. Exemplary additional active agents include, but are not limited to, antihistamines (including H1, H3 and H4 receptor antagonists), steroids, bronchodialators, anti-inflammatory agents, anti-inflammatory agents (e.g., leukotriene inhibitors and antagonists), decongestants, expectorants, non-steroidal anti-inflammatory agents (NSAIDs), non-steroidal immunophilin-dependent immunosuppressants (NsIDIs), anticholinergic agents, COX-2 inhibitors, anti-fungal agents, anti-infective agents, mucolytic agents, mast cell stabilizers, non-antibiotic anti-microbial agents, anti-viral agents, antiseptics, neurokinin antagonists, platelet activating factor (PAF) and 5-lipoxygenase (5-LO) inhibitors.

Examples of antihistamines suitable for inclusion in the pharmaceutical compositions utilized in the present methods include, but are not limited to, acrivastine, azelastine, cyclizine, carebastine, cyproheptadine, carbinoxamine, doxylamine, dimethindene, ebastine, epinastine, efletirizine, ketotifen, levocabastine, mizolastine, mequitazine, mianserin, noberastine, meclizine, norastemizole, olopatadine, picumast, tripelenamine, temelastine, trimeprazine, triprolidine, bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine, pyrilamine, astemizole, terfenadine, loratadine, cetirizine, levocetirizine, fexofenadine, descarboethoxyloratadine, desloratadine, dimenhydrinate and hydroxyzine.

Examples of H3 receptor antagonists suitable for inclusion in the pharmaceutical compositions utilized in the present methods include, but are not limited to, thioperamide, impromidine, burimamide, clobenpropit, impentamine, mifetidine, clozapine, S-sopromidine. R-sopromidine and ciproxifam.

Examples of steroids suitable for inclusion in the pharmaceutical compositions utilized in the present methods include corticosteroid anti-inflammatory agents. Examples of inhaled corticosteroids include fluticasone (Flovent®), budesonide (Pulmicort®), flunisolide (AeroBid®), triamcinolone (Azmacort®, Nasacort®, Atlone®) and beclomethasone (Beclovent®, Vaceril®, and Vancenase®). Examples of oral corticosteroids (pill/tablet form) are prednisone (Deltasone®, Meticorten®, or Paracort®), methylprednisolone (Medrol®) and prednisolone (Delta Cortef® and Sterane®). The oral corticosteroids (liquid form) are Pedipred® and Prelone®. Additional examples of steroids suitable for inclusion in the present methods include but are not limited to, fluoromethalone, fluticasone, mometasone, triamcinolone, betamethasone, flunisolide, budesonide, beclomethasone, budesonide, rimexolone, beloxil, prednisone, loteprednol, dexamethasone and its analogues (e.g., dexamethasone beloxil).

Examples of bronchodilators suitable for inclusion in the pharmaceutical compositions utilized in the present methods include, but are not limited to, metaproterenol (Alupent®, Metaprel®), ephedrine, terbutaline (Brethaire®) and albuterol (Proventil®, Ventolin®). These drugs are inhaled and are used to relieve symptoms during acute asthma attacks. Examples of long-acting bronchodilators include salmeterol (Serevent®), metaproterenol (Alupent®) and theophylline (Aerolate®, Bronkodyl®, Slo-phyllin®, and Theo-Dur®) and aminophylline.

Examples of anti-inflammatory medicaments suitable for inclusion in the pharmaceutical compositions utilized in the present methods include leukotriene inhibitors and antagonists. Zafirlukast (Accolate®), montelukast (Singulair®) and zileuton (Zyflo®) belong to this class of agents. These drugs are administered orally and inhibit leukotrienes from binding to smooth muscle cells lining the airways. Other inhaled anti-inflammatory drugs include cromolyn sodium (Intal®) and nedrocromil (Tilade®).

Examples of leukotriene antagonists (e.g., leukotriene D4 antagonists) suitable for inclusion in the pharmaceutical compositions utilized in the present methods include, but are not limited to, albuterol sulfate, aminophylline, amoxicillin, ampicillin, astemizole, attenuated tubercle bacillus, azithromycin, bacampicillin, beclomethasone dipropionate, budesonide, bupropion hydrochloride, cefaclor, cefadroxil, cefixime, cefprozil, cefuroxime axetil, cephalexin, ciprofloxacin hydrochloride, clarithromycin, clindamycin, cloxacillin, doxycycline, erythromycin, ethambutol, fenoterol hydrobromide, fluconazole, flunisolide, fluticasone propionate, formoterol fumarate, gatifloxacin, influenza virus vaccine, ipratropium bromide, isoniazid, isoproterenol hydrochloride, itraconazole, ketoconazole, ketotifen, levofloxacin, minocycline, montelukast (e.g., montelukast sodium), moxifloxacin, nedocromil sodium, nicotine, nystatin, ofloxacin, orciprenaline, oseltamivir, oseltamivir sulfate, oxtriphylline, penicillin, pirbuterol acetate, pivampicillin, pneumococcal conjugate vaccine, pneumococcal polysaccharide vaccine, prednisone, pyrazinamide, rifampin, salbutamol, salmeterol xinafoate, sodium cromoglycate (cromolyn sodium), terbutaline sulfate, terfenadine, theophylline, triamcinolone acetonide, zafirlukast and zanamivir.

Examples of decongestants suitable for inclusion in the pharmaceutical compositions utilized in the present methods include, but are not limited to, pseudoephedrine, phenylephedrine, phenylephrine, phenylpropanolamine, oxymetazoline, propylhexedrine, xylometazoline, epinephrine, ephedrine, desoxyephedrine, naphazoline, and tetrahydrozoline.

Examples of expectorants suitable for inclusion in the pharmaceutical compositions utilized in the present methods include, but are not limited to, guaifenesin, codeine phosphate, and isoproternol hydrochloride.

Examples of NSAIDs suitable for inclusion in the pharmaceutical compositions utilized in the present methods include, but are not limited to, ibuprofen, aceclofenac, diclofenac, naproxen, etodolac, flurbiprofen, fenoprofen, ketoprofen, suprofen, fenbufen, fluprofen, tolmetin sodium, oxaprozin, zomepirac, sulindac, indomethacin, piroxicam, mefenamic acid, nabumetone, meclofenamate sodium, diflunisal, flufenisal, piroxicam, ketorolac, sudoxicam and isoxicam.

Examples of NsIDIs suitable for inclusion in the pharmaceutical compositions utilized in the present methods include, but are not limited to, calcineurin inhibitors, such as cyclosporine, tacrolimus, ascomycin, pimecrolimus, as well as other agents (peptides, peptide fragments, chemically modified peptides, or peptide mimetics) that inhibit the phosphatase activity of calcineurin. NsIDIs also include rapamycin (sirolimus) and everolimus, which bind to an FK506-binding protein, FKBP-12, and block antigen-induced proliferation of white blood cells and cytokine secretion.

Examples of anticholinergics suitable for inclusion in the pharmaceutical compositions utilized in the present methods include, but are not limited to, ipratropium (Atrovent®), atropine, and scopolamine.

Examples of COX-2 inhibitors for inclusion in the pharmaceutical compositions utilized in the present methods include, but are not limited to, rofecoxib, celecoxib, valdecoxib, lumiracoxib, meloxicam, and nimesulide.

Examples of mast cell stabilizers suitable for inclusion in the pharmaceutical compositions utilized in the present methods include, but are not limited to, cromolyn and nedocromil sodium.

Examples of anti-fungal agents suitable for inclusion in the pharmaceutical compositions utilized in the present methods include, but are not limited to, amphotericin B, nystatin, fluconazole, ketoconazole, terbinafine, itraconazole, imidazole, triazole, ciclopirox, clotrimazole, and miconazole.

Examples of anti-infective agents suitable for inclusion in the pharmaceutical compositions utilized in the present methods include, but are not limited to, penicillins and other beta lactam antibiotics, cephalosporins, macrolides, ketolides, sulfonamides, quinolones, aminoglycosides, and linezolid.

Examples of non-antibiotic antimicrobials suitable for inclusion in the pharmaceutical compositions utilized in the present methods include, but are not limited to, taurolidine.

Examples of antibiotic agents suitable for inclusion in the pharmaceutical compositions utilized in the present methods include, but are not limited to, cefuroxime, vancomycin, amoxicillin and gentamicin.

Examples of antiseptics suitable for inclusion in the pharmaceutical compositions utilized in the present methods include, but are not limited to, iodine, chlorhexidine acetate, sodium hypochlorite, and calcium hydroxide.

Examples of neurokinin antagonists suitable for inclusion in the pharmaceutical compositions utilized in the present methods include, but are not limited to, oximes, hydrazones, piperidines, piperazines, aryl alkyl amines, hydrazones, nitroalkanes, amides: isoxazolines, quinolines, isoquinolines, azanorbornanes, naphthyridines, and benzodiazepines.

Examples of 5-lipoxygenase (5-LO) inhibitors suitable for inclusion in the pharmaceutical compositions utilized in the present methods include, but are not limited to, zileuton, docebenone, piripost and tenidap.

ILLUSTRATIVE EMBODIMENTS

The following embodiments are illustrative and are not intended to limit the disclosed subject matter.

Embodiment 1

A method of treating or preventing a pulmonary disease or disorder in a subject comprising administering an effective amount of a compound that modulates Calmodulin Kinase II (CaMKII) activity, thereby treating or preventing the pulmonary disease or disorder in the subject.

Embodiment 2

The method of embodiment 1, wherein the compound inhibits CaMKII activity.

Embodiment 3

The method of embodiment 1 or 2, wherein the pulmonary disease or disorder is asthma.

Embodiment 4

The method of any of embodiments 1-3, wherein the compound is an aryl-indolyl maleimide.

Embodiment 5

The method of embodiment 4, wherein the compound is an aryl-indolyl maleimide listed in any of Tables 1-14, or an analog or derivative thereof that inhibits CaMKII.

Embodiment 6

The method of any of embodiments 1-5, wherein the compound inhibits the delta isoform of CaMKII.

Embodiment 7

The method of any of embodiments 1-3, wherein the compound is KN-93 or an analog or derivative thereof that inhibits CaMKII.

Embodiment 8

The method of any of embodiments 1-3, wherein the compound is a peptide.

Embodiment 9

The method of any of embodiments 1-8, wherein the compound is administered in a dose of from about 0.05 mg to about 5.0 mg per kilogram of body weight of the subject.

Embodiment 10

The method of any of embodiments 1-8, wherein the compound is administered in a dose of from about 0.3 mg to about 3.0 mg per kilogram of body weight of the subject.

Embodiment 11

The method of any of embodiments 1-10, wherein the compound is administered in a sustained release form, an inhaled form, or an oral form.

Embodiment 12

The method of embodiment 11, wherein the compound is administered intravenously.

Embodiment 13

The method of embodiment 11, wherein the compound is administered by inhalation.

Embodiment 14

The method of embodiment 13, wherein the effective amount is between about 0.5 and about 500 µg inhaled compound per day.

Embodiment 15

The method of embodiment 11, wherein the compound is administered in an oral form selected from the group consisting of tablets and capsules.

Embodiment 16

The method of any of embodiments 1-15, wherein pain or other symptom associated with asthma is reduced, eliminated or prevented.

Embodiment 17

The method of any of embodiments 1-15, wherein the subject is a mammal.

Embodiment 18

The method of embodiment 17, wherein the mammal is a human.

Embodiment 19

The method of any of embodiments 1-18, wherein the effective amount is at least 1.0 ng/kg of body weight.

Embodiment 20

A pharmaceutical composition formulated for pulmonary delivery and comprising an effective amount of a compound that modulates CaMKII for treating a pulmonary disease or disorder.

Embodiment 21

A method of treating or preventing a pulmonary disease or disorder in a subject comprising administering an effective amount of a therapeutic agent that modulates methionine sulfoxide reductase (Msr) activity or expression in the patient, either directly or indirectly, thereby treating or preventing the pulmonary disease or disorder in the subject.

Embodiment 22

The method of embodiment 21, wherein the therapeutic agent increases Msr activity or expression and subsequently augments the conversion of oxidized methionines in CaMKII to non-oxidized methionines thereby modulating or inhibiting CaMKII activity.

Embodiment 23

The method of embodiment 22, wherein the therapeutic agent increases Msr activity or expression and subsequently augments the conversion of oxidized methionine residues present at amino acid positions 281 and 282 of CaMKII to non-oxidized states, thereby modulating or inhibiting CaMKII activity.

Embodiment 24

The method of any of embodiments 21-23, wherein the pulmonary disease or disorder is asthma.

Embodiment 25

The method of any of embodiments 21-24, wherein the therapeutic agent is administered in a dose of from about 0.05 mg to about 5.0 mg per kilogram of body weight of the subject.

Embodiment 26

The method of any of embodiments 21-25, wherein the therapeutic agent is administered in a dose of from about 0.3 mg to about 3.0 mg per kilogram of body weight of the subject.

Embodiment 27

The method of any of embodiments 21-26, wherein the therapeutic agent is administered in a sustained release form, an inhaled form, or an oral form.

Embodiment 28

The method of embodiment 27, wherein the therapeutic agent is administered intravenously.

Embodiment 29

The method of embodiment 27, wherein the therapeutic agent is administered by inhalation.

Embodiment 30

The method of embodiment 29, wherein the effective amount is between about 5 and about 500 µg inhaled compound per day.

Embodiment 31

The method of embodiment 27, wherein the compound is administered in an oral form selected from the group consisting of tablets and capsules.

Embodiment 32

The method of any of embodiments 21-31, wherein pain or other symptom associated with asthma is reduced, eliminated or prevented.

Embodiment 33

The method of any of embodiments 21-32, wherein the subject is a mammal.

Embodiment 34

The method of embodiment 33, wherein the mammal is a human.

Embodiment 35

The method of any of embodiments 21-34, wherein the effective amount is at least 1.0 ng/kg of body weight.

Embodiment 36

A pharmaceutical composition comprising an effective amount of a therapeutic agent that modulates methionine sulfoxide reductase (Msr) activity or expression in a patient for treating a pulmonary disease or disorder.

Embodiment 37

A method of treating or preventing a pulmonary disease or disorder in a subject comprising administering an effective amount of a therapeutic agent that modulates NADPH oxidase activity or expression in the patient, either directly or indirectly, thereby treating or preventing the pulmonary disease or disorder in the subject.

Embodiment 38

The method of embodiment 37, wherein the therapeutic agent inhibits NADPH oxidase activity and subsequently inhibits the oxidation of methionines in CaMKII thereby modulating or inhibiting CaMKII activity.

Embodiment 39

The method of embodiment 38, wherein the therapeutic agent inhibits NADPH oxidase activity and subsequently inhibits the oxidation of methionine residues present at amino acid positions 281 and 282 of CaMKII, thereby modulating or inhibiting CaMKII activity.

Embodiment 40

The method of any of embodiments 37-39, wherein the pulmonary disease or disorder is asthma.

Embodiment 41

The method of any of embodiments 37-40, wherein the therapeutic agent is administered in a dose of from about 0.05 mg to about 5.0 mg per kilogram of body weight of the subject.

Embodiment 42

The method of any of embodiments 37-41, wherein the therapeutic agent is administered in a dose of from about 0.3 mg to about 3.0 mg per kilogram of body weight of the subject.

Embodiment 43

The method of any of embodiments 37-42, wherein the therapeutic agent is administered in a sustained release form, an inhaled form, or an oral form.

Embodiment 44

The method of embodiment 43, wherein the therapeutic agent is administered intravenously.

Embodiment 45

The method of embodiment 43, wherein the therapeutic agent is administered by inhalation.

Embodiment 46

The method of embodiment 45, wherein the effective amount is between about 5 and about 500 µg inhaled compound per day.

Embodiment 47

The method of embodiment 43, wherein the compound is administered in an oral form selected from the group consisting of tablets and capsules.

Embodiment 48

The method of any of embodiments 37-47, wherein pain or other symptom associated with asthma is reduced, eliminated or prevented.

Embodiment 49

The method of any of embodiments 37-48, wherein the subject is a mammal.

Embodiment 50

The method of embodiment 49, wherein the mammal is a human.

Embodiment 51

The method of any of embodiments 37-50, wherein the effective amount is at least 1.0 ng/kg of body weight.

Embodiment 52

The method of any of embodiments 37-51, wherein the therapeutic agent is an inhibitor of NADPH oxidase activity and is selected from a group consisting of apocynin, diphenylene iodoniumchloride (DPI), staurosporine, phenyl arsine oxide (PAO), 4-(2-Aminoethyl)-benzenesulfonyl fluoride (AEBSF), gp91ds-tat, PR-39, VAS2870 [3-bezyl-7-(2-benzoxazolyl)thio-1,2,3-triazolo(4,5-d)pyrimidine], and S17834 [6,8-diallyl 5,7-dihydroxy 2-(2-allyl 3-hydroxy 4-methoxyphenyl)1-H benzo(b)pyran-4-one].

Embodiment 53

A pharmaceutical composition formulated for pulmonary delivery and comprising an effective amount of a therapeutic agent that modulates NADPH oxidase activity or expression in a patient for treating a pulmonary disease or disorder.

Embodiment 54

The composition of claim 53, wherein the therapeutic agent is an inhibitor of NADPH oxidase activity and is selected from a group consisting of apocynin, diphenylene iodoniumchloride (DPI), staurosporine, phenyl arsine oxide (PAO), 4-(2-Aminoethyl)-benzenesulfonyl fluoride (AEBSF), gp91ds-tat, PR-39, VAS2870 [3-bezyl-7-(2-benzoxazolyl)thio-1,2,3-triazolo(4,5-d)pyrimidine], and S17834 [6,8-diallyl-5,7-dihydroxy 2-(2-allyl 3-hydroxy 4-methoxyphenyl)1-H benzo(b)pyran-4-one].

EXAMPLES

The following Examples are illustrative and are not intended to limit the disclosed subject matter.

CaMKII Signaling in Asthma and Treatment by Inhibition of CaMKII

Background and Introduction

Asthma is a disease of airway smooth muscle (ASM) dysfunction that affects approximately 30 million Americans. The incidence of asthma has increased markedly and leads to significant morbidity and mortality with estimated healthcare and lost opportunity costs of 10.7 billion dollars annually in the United States. (See Weiss et al., 2000). Improved therapies are necessary to reduce suffering and lost productivity in asthma patients. Smooth muscle hypertrophy, hyper-reactivity, pathological remodeling, airway obstruction and inflammation are well-established disease factors in asthma patients, but none of the presently exploited therapeutic targets operates simultaneously on each of these pathways to reduce asthma symptoms. Present therapies are focused on 'upstream' targets, such as G-protein-coupled receptors (e.g., histamine, adrenergic, leukotriene) glucocorticoid receptors and reactive oxygen species that activate signaling pathways important for selective smooth muscle responses in asthma. Here, 'downstream' targets that integrate inputs from multiple upstream targets were studied, where downstream targets are more likely to affect diverse asthma phenotypes in bronchiolar epithelium and smooth muscle and so prove to be superior drug targets for reducing asthma. In particular, the results presented here demonstrate that calmodulin kinase II (CaMKII) is a key downstream determinant of critical asthma-related smooth muscle phenotypes (FIG. 1). These findings demonstrate that CaMKII contributes to bronchial hyper-reactivity in vivo and that CaMKII activates hypertrophic and proinflammatory gene programs. These findings also suggest that CaMKII activity may be modulated in a subject in order to treat asthma.

Figure 2:
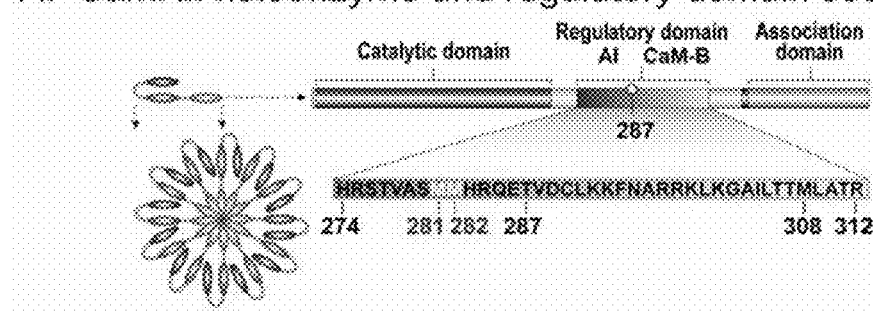
FIG. 2. CaMKII activity is sustained and made $Ca^{2+}$-independent by T287 autophosphorylation and by M281/282 oxidation. A. The CaMKII holoenzyme is assembled by monomers interconnected at the C terminus. B. & C, CaMKII is initially activated by $Ca^{2+}$/CaM binding, but CaMKII activity is sustained by autophosphorylation and oxidation at defined residues in the regulatory domain.
Figure 2:
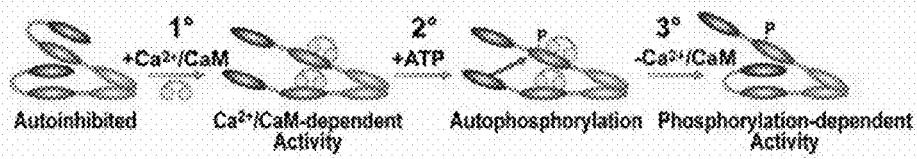
Figure 2:
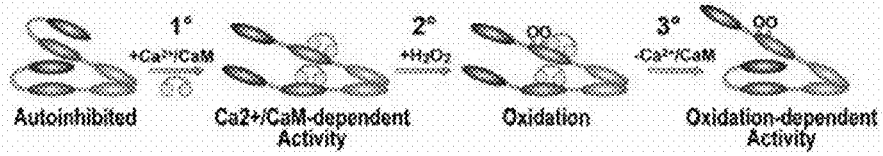

CaMKII is a serine/threonine kinase that was originally identified by its dependence on calcified calmodulin ($Ca^{2+}$/CaM) for activation (FIG. 2). CaMKII is abundant in all excitable tissues. (See Pfleiderer et al., 2004). The CaMKII holoenzyme is a dodecamer (joined together by the C terminus association domain). (See Hudmon and Schulman. 2002). $Ca^{2+}$/CaM binding to the CaMKII regulatory domain disrupts a basal inhibitory interaction between a pseudo substrate motif and the catalytic domain, leading to CaMKII activation (FIG. 2A). $Ca^{2+}$/CaM binding exposes a conserved Thr (287 in CaMKIIδ) that can be autophosphorylated by adjacent CaMKII monomers within the holoenzyme, leading to sustained $Ca^{2+}$/CaM-independent CaMKII activity (FIG. 2B). More recently, a ROS pathway for CaMKII was identified. (See Howe et al., 2004).

Reactive oxygen species (ROS) are key signaling molecules in health and disease. In asthma ROS are linked to airway inflammation and are known to be increased in the exhaled breath of asthmatics. Calcium/calmodulin-dependent protein kinase II (CaMKII) is a multi functional protein believed to connect up-stream pro-oxidant environments to down-stream cellular responses such as hypertrophy and inflammation. Although initial activation is through binding of calcified calmodulin ($Ca^{2+}$/CaM), secondary methionine oxidation induces CaMKII to become active even in the absence of $Ca^{2+}$/CaM binding. The role of CaMKII in asthma is not yet well understood, but it is hypothesized that excessive CaMKII activation due to increased levels of ROS in asthma may contribute to airway remodeling, airway hyperactivity and inflammation in asthma.

Oxidation of paired Met residues in the CaMKII regulatory domain has been shown to be a molecular mechanism for ROS activation. (See Erickson et al., 2008). The oxidant susceptible Met residues (281/282) are near to the autophosphorylation site (Thr 287) and data supports a concept that Met oxidation and Thr 287 autophosphorylation convert CaMKII into a $Ca^{2+}$/CaM independent species by a shared mechanism, whereby the bulky negative charges (from autophosphorylation or oxidation) prevent inactivation by inhibiting re-association of the kinase domain and pseudo-substrate motif (FIG. 2C). Like autophosphorylation, Met oxidation requires initial $Ca^{2+}$/CaM binding that leads to sustained $Ca^{2+}$/CaM activity.

The data presented here implicate ROS production by NADPH oxidases in the progression of asthma, while the antioxidant activity of MsrA appears critical in suppressing airway inflammation and remodeling. This study also introduces a new model of epithelial CaMKII inhibition and provides data suggesting that CaMKII is a novel therapeutic target for asthma.

Specific Aims

In this example, specific aims included: (1) Testing whether CaMKII activation contributes to abnormal $Ca^{2+}_i$ homeostasis and mechanical dysfunction in airway smooth muscle (ASM); (2) Measuring the contribution of upstream redox signaling to CaMKII activation in ASM; (3) Determining whether a CaMKII and MEF2 (myocyte-specific enhancement factor 2) pathway is important for hypertrophy in ASM; and (4) Determining whether CaMKII increases expression of inflammatory genes in ASM by activating NF-κβ.

Methods and Results

Determining the Localization of CaMKII in the Lung.

Figure 3:
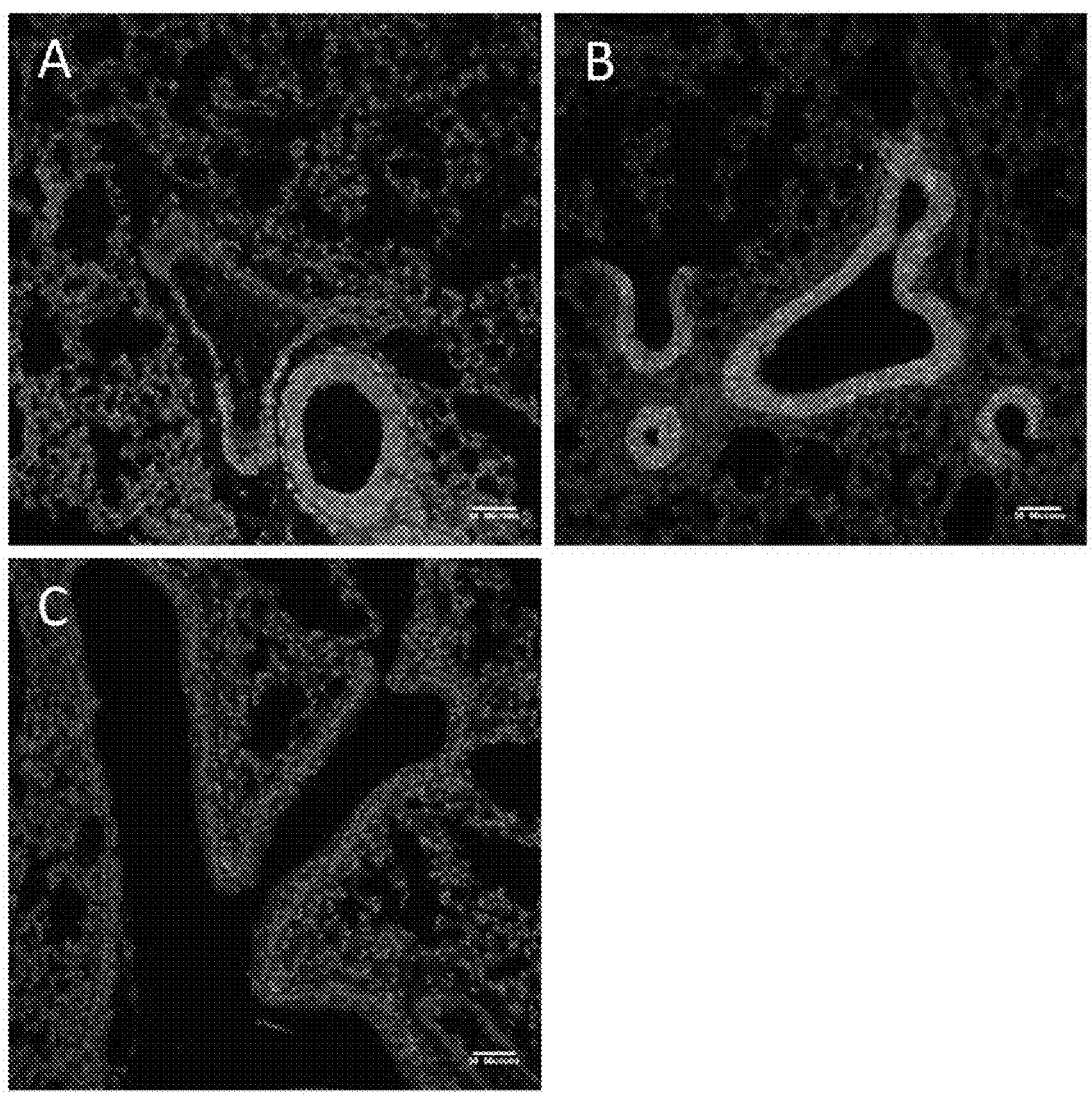
FIG. 3. Immunofluorescent staining for CaMKII in lung tissue. Sections of lung tissue from wild type mice were stained with antibodies for (A) total CaMKII. (B) oxidized CaMKII, and (C) active phosphorylated CaMKII. Total CaMKII was detected in respiratory epithelium and smooth muscle cells, oxidized CaMKII in epithelium and phosphorylated CaMKII in smooth muscle cells. Representative sections are shown.

To investigate the potential role of CaMKII in asthma, CaMKII was localized in airways. Total CaMKII was present in the epithelium and smooth muscle of the airway, but oxidized CaMKII was preferentially localized to the respiratory epithelium (FIG. 3). The present findings suggest that ROS and methionine oxidation are important in mediating inflammation and remodeling in the asthmatic airway. CaMKII is activated by phosphorylation but also may be activated by ROS via methionine oxidation.

Animal Model for Asthma and Effects of Inhaled KN-93 on Asthma.

In order to test the concept that CaMKII inhibition can reduce asthma symptoms, a validated asthma model was utilized. This model induces airway inflammation and hyper-reactivity by intra-peritoneal sensitization and inhalational challenge with the experimental allergen, ovalbumin. The "asthmatic" mice are then characterized by a graded inhalational challenge protocol using aerosolized methacholine. (See Jain et al., 2003). This approach is similar to that used in humans with clinical asthma.

Figure 4:
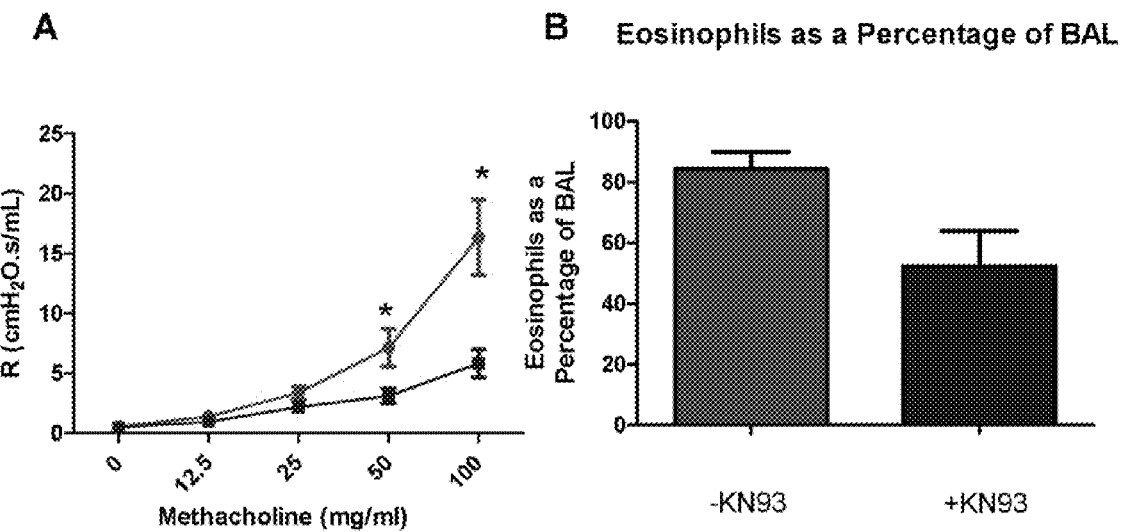
FIG. 4. Effects of inhaled KN-93 on asthma. (A) C6B2 mice were sensitized by two i.p. injections of ovalbumin, followed by three 30 min inhalations of ovalbumin in the presence or absence of the CaMKII inhibitor KN93 (100 μM) intranasal. Airway reactivity was determined by Methacholine challenge using the Flexivent-measured airway resistance as the readout. (B) Bronchoalveolar lavage eosinophils in mice treated with KN 93 compared with untreated control mice.

C6B2 mice were sensitized by two i.p. injections of ovalbumin, followed by three 30 min inhalations of ovalbumin in the presence or absence of the CaMKII inhibitor KN93 (100 mM) intranasal. Airway reactivity was determined by Methacholine challenge using the Flexivent-measured airway resistance as the readout. A significant reduction in airway resistance was seen at 50 and 100 µg/ml Methacholine in the mice treated with the CaMKII inhibitor. (* $p<0.05$, n=4 per group) (FIG. 4A). Bronchoalveolar lavage eosinophils (a measure of allergic airway inflammation) were reduced in mice treated with KN 93 compared with untreated control mice (FIG. 4B).

Investigating the Role of Oxidized CaMKII in the Respiratory Epithelium.

Figure 5:
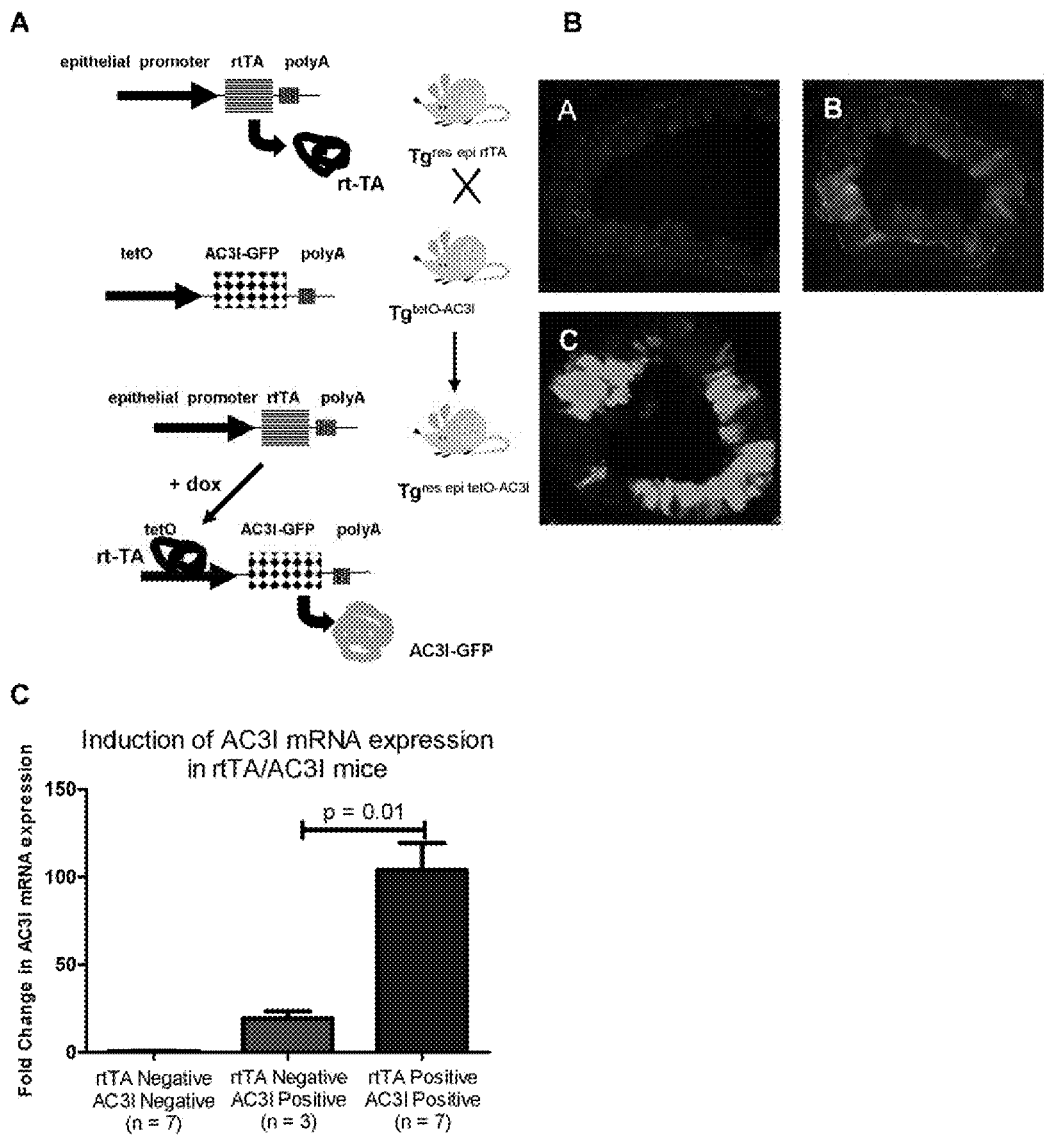
FIG. 5. Mouse model of doxycycline-inducible, respiratory epithelium-delimited expression of the CaMKII peptide inhibitor AC3I. (A) Transgenic mice with the transgene for a green fluorescent protein (GFP)-coupled CaMKII inhibitor peptide AC3I (Tg tetO-AC3I) under the regulation of a tetracycline-responsive promoter are crossed with transgenic mice that express the reverse tetracycline-controlled transactivator (rtTA) protein driven by a respiratory epithelium-specific promoter (Tg res epi rtTA). In the double transgenic Tg res epi tetO-AC3I mice, transgene expression can be induced by feeding doxycycline with chow or drinking water. (B) Immunofluorescence for the GFP-labeled CaMKII inhibitor AC3I. (A) No GFP is detected in the respiratory epithelium of control mice. (B) In Tg tetO-AC3I, low levels of green fluorescent protein are detected. (C) In mice that carry both transgenes, strong expression of the green fluorescent protein-labeled CaMKII inhibitor AC3I is noted after feeding doxycyclin for 2 weeks. (C) The induction of the green fluorescent protein-labeled CaMKII inhibitor AC3I was determined by real time PCR. More than 100-fold induction of green fluorescent protein-labeled CaMKII inhibitor AC3I is noted.

To investigate the contribution of CaMKII to asthma, transgenic mice were created. These mice have inducible expression of GFP tagged AC3-I (a selective CaMKII inhibitor) in the respiratory epithelium, upon administration of doxycycline. These mice were created by crossing mice expressing GFP-AC3-I with mice expressing the reverse tetracycline transactivator (rtTA) under the control of a clara cell secretory protein promoter (CCSP), which is expressed specifically in the respiratory epithelium (FIG. 5A). The interbred mice were fed chow supplemented with 2.5 mg/kg doxycycline for 3 weeks before beginning ovalbumin challenge. Significant expression of AC3-I was induced and was localized to the respiratory epithelium (FIGS. 5B and 5C).

Mice Expressing the CaMKII Inhibitor AC3-I in Respiratory Epithelium Show Reduced Airway Hyper-Reactivity and Decreased Inflammatory Infiltrate.

Figure 6:
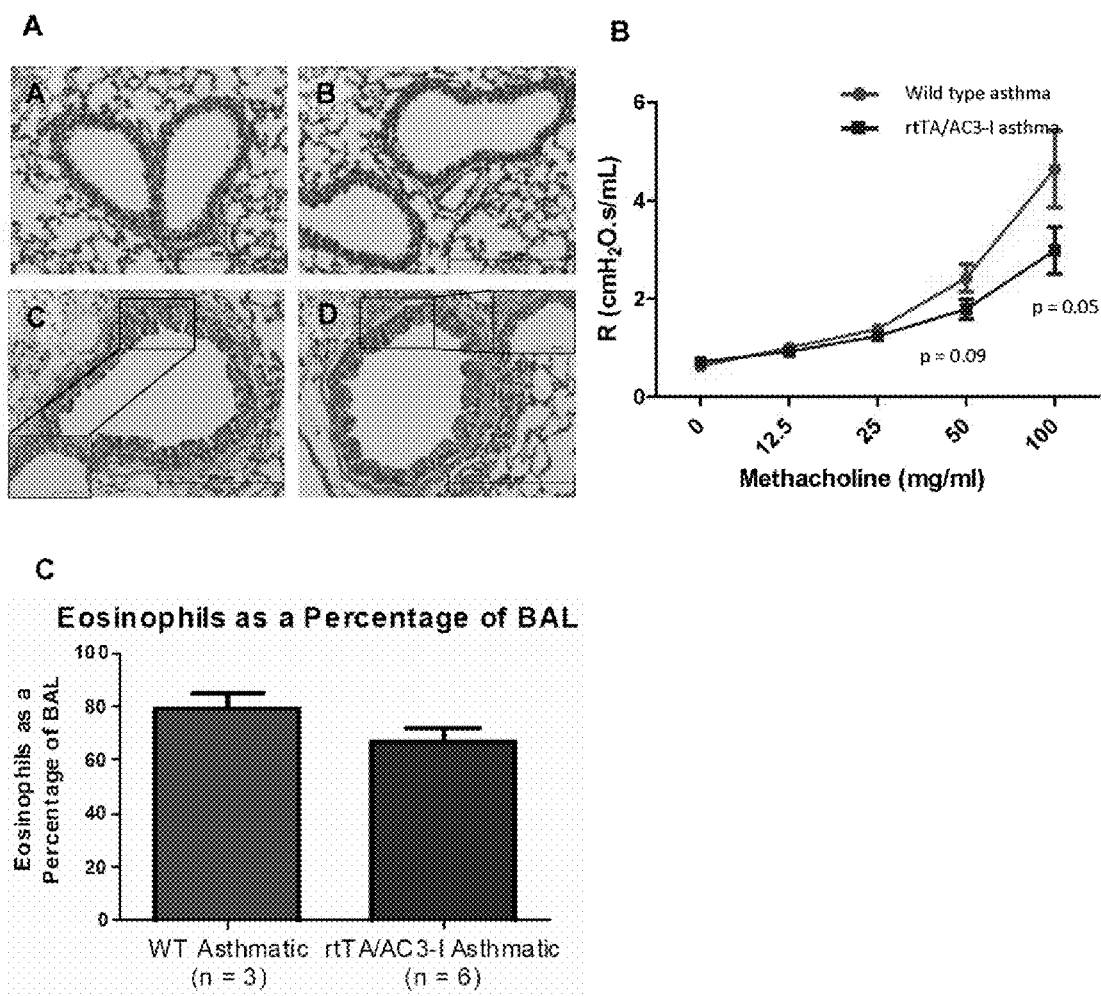
FIG. 6. Effects of inducible, endothelial-targeted genetic CaMKII inhibition (rt TA/AC3-I mice) on asthma. A (A) The alcian blue, periodic acid/Schiff (PAS) stain shows increased mucous in ovalbumin-sensitized WT mice (B) compared to baseline (A). The increase in mucous by ovalbumin sensitization is reduced in rtTA/AC3-1 mice with epithelial CaMKII inhibition sensitized with ovalbumin (D)-compare to (C). B Wild type control and mice with respiratory epithelium-delimited expression of the CaMKII peptide inhibitor AC3I (rtTA/AC3I-mice) were sensitized by two i.p. injections of ovalbumin, followed by three 30 min inhalations of ovalbumin. Air way resistance was determined by Methacholine challenge. A significant reduction in airway resistance was seen in mice with endothelial-targeted genetic CaMKII inhibition. C BAL eosinophil count in wild type and rtTA/AC3-I mice.

Mice expressing AC3-I in the respiratory epithelium were subjected to ovalbumin challenge. Mice expressing AC3-I exhibited improved airway histology, with decreased occurrence of mucus gland hyperplasia (FIG. 6A), decreased airway hyper-reactivity after challenge with methacholine (FIG. 6B) and decreased infiltration by eosinophils (FIG. 6C).

p47 Activity Lays an Important Role in the Pathogenesis of Asthma.

Figure 7:
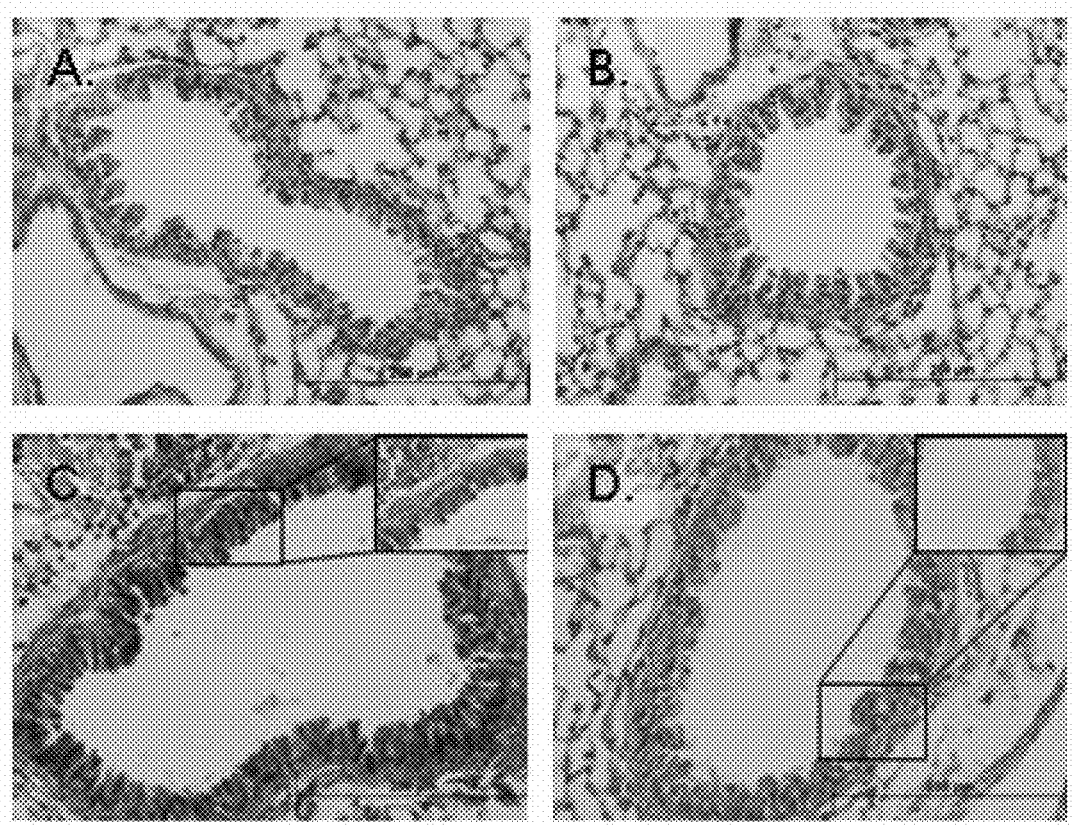
FIG. 7. Alcian Blue/PAS stain showing mucus distribution in the airway of p47$^{-/-}$ lacking a functional NAPDH oxidase (types 1 and 2) and wild type mice (×200). Staining represents acidic and neutral mucus. A. WT healthy, B. p47$^{-/-}$ healthy. C. WT asthmatic. D. p47$^{-/-}$ asthmatic. Inserts in C and D show magnified sections (×400).
Figure 8:
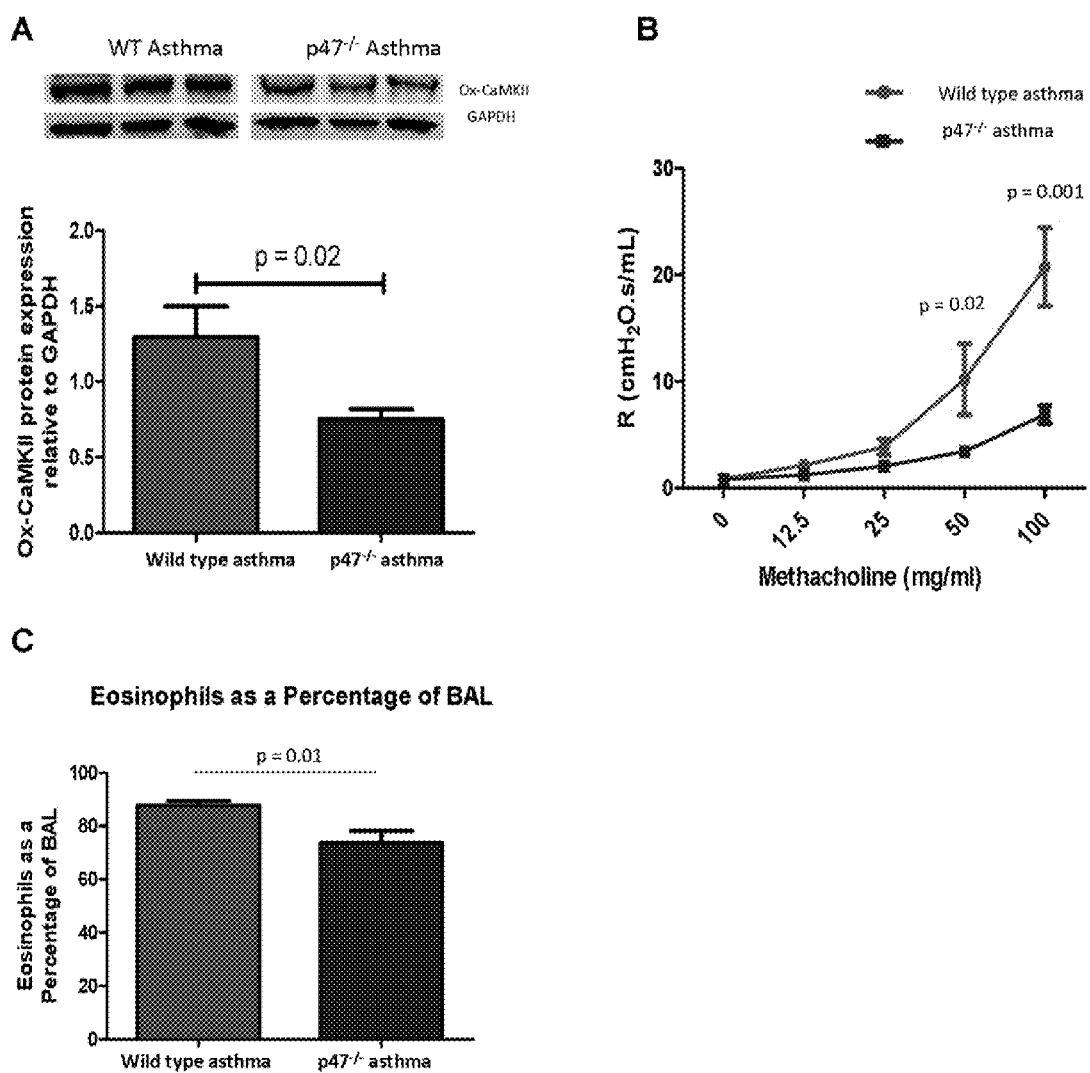
FIG. 8. Effects of NADPH oxidase inhibition by gene deletion (p47$^{-/-}$) (A) 20 μg protein isolated from lungs of wild type and p47$^{-/-}$ mice were separated and blotted for oxidized CaMKII. GAPDH blots were performed as loading control. Densitometry of 3 independent blots shows a significant decrease in oxidized CaMKII in p47$^{-/-}$ mice. (B) Wild type control and p47$^{-/-}$ mice underwent ovalbumin sensitization as described herein. Airway hyper-reactivity measured as resistance was tested by Methacholine challenge. A significant decrease in airway resistance was detected in p47$^{-/-}$ mice. (C) Eosinophil counts in wild type controls and p47$^{-/-}$ mice reveal significantly lower cell numbers in p47$^{-/-}$ mice.

Ovalbumin sensitized $p47^{-/-}$ mice were observed to exhibit decreased mucus gland metaplasia (FIG. 7). In addition. CaMKII protein levels in $p47^{-/-}$ and asthmatic mice were observed to correlate with asthma severity. The levels of oxidized CaMKII in whole lung protein lysates obtained from $p47^{-/-}$ and WT asthmatic mice was measured (FIG. 8A). The data show that the levels of oxidized CaMKII correlate with the severity of asthma—being significantly decreased in the lungs of $p47^{-/-}$ asthmatic mice. In addition, ovalbumin sensitized $p47^{-/-}$ mice were observed to exhibit decreased airway hyper-reactivity (FIG. 8B) and decreased recruitment of eosinophils to the airway (FIG. 8C). These data suggest that CaMKII has an important regulatory role in the asthmatic airway and that p47-derived ROS are a key component in mediating the pathogenesis of asthma.

Methionine Oxidation Exacerbates Airway Remodeling and the Recruitment of Eosinophils into the Airway.

Figure 9:
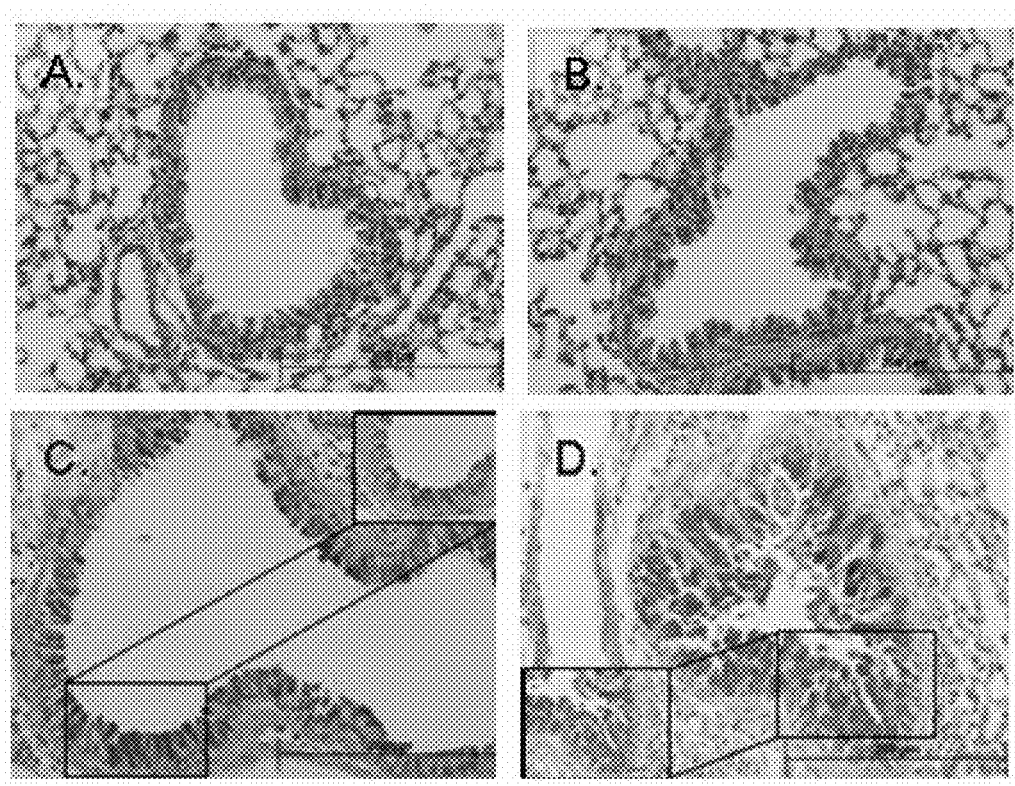
FIG. 9. Alcian Blue/PAS stain showing mucus distribution in the airway of MsrA$^{-/-}$ and wild type mice (×200). Staining represents acidic and neutral mucus. A. WT healthy. B. MsrA$^{-/-}$ healthy. C. WT asthmatic. D. MsrA$^{-/-}$ asthmatic. Inserts in C and D show magnified sections (×400).
Figure 10:
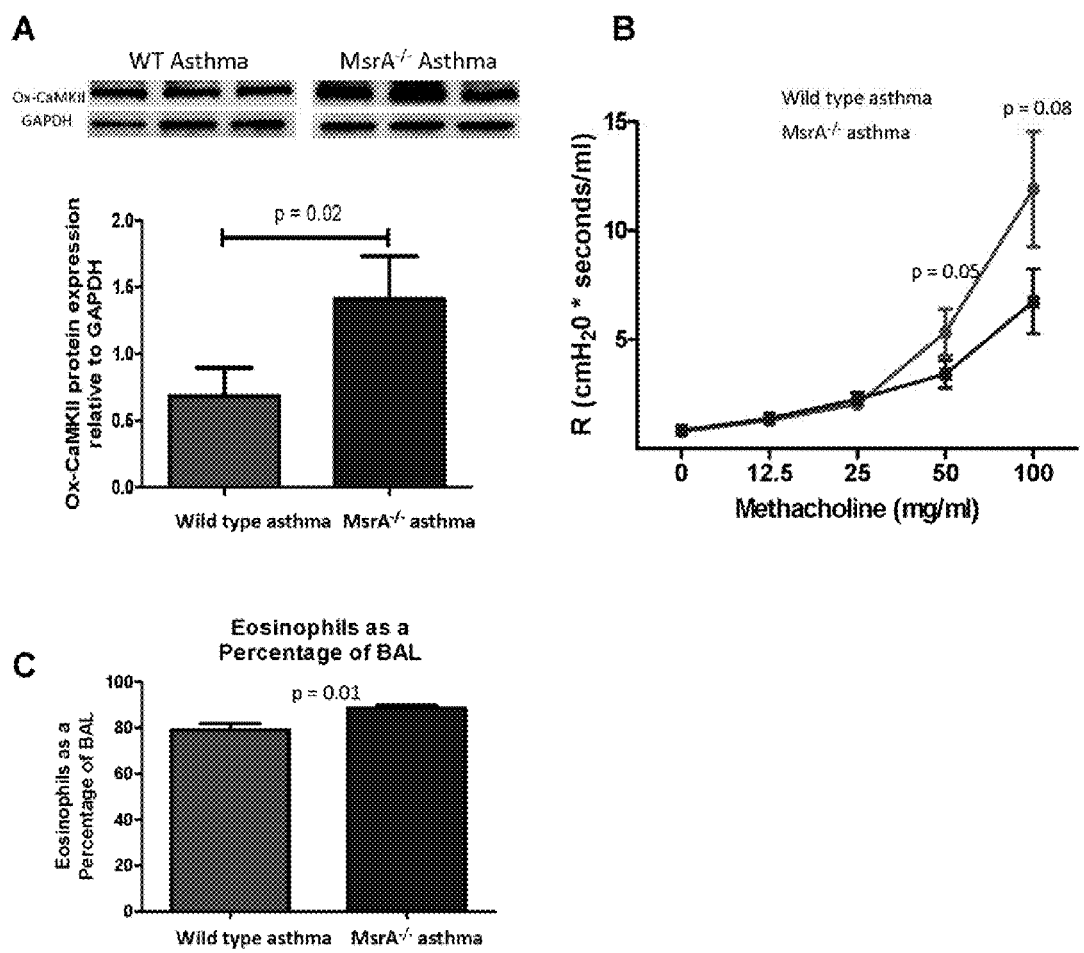
FIG. 10. Effects of MsrA inhibition by gene deletion (MsrA$^{-/-}$). (A) 20 μg protein isolated from wild type controls or MsrA$^{-/-}$ mice were blotted for oxidized CaMKII. GAPDH blots were performed as loading control. Densitometry was performed in 3 independent blots. Significantly higher levels of oxidized CaMKII were detected in MsrA$^{-/-}$ mice. (B) Ovalbumin sensitization of airways was performed as described herein. Airway resistance was determined by Methacholine challenge. Significantly higher airway resistance was found in MsrA$^{-/-}$ mice. (C) Higher eosinophil cell counts were detected in the bronchoalveolar lavage of MsrA$^{-/-}$ mice.

Methionine sulfoxide reductase A (MsrA) is a widely expressed enzyme able to reduce oxidized methionines in a range of proteins to maintain tissue homeostasis. Ovalbumin sensitized $MsrA^{-/-}$ mice were observed to exhibit increased mucus gland metaplasia (FIG. 9). In order to determine whether methionine oxidation plays a role in the progression of asthma, levels of oxidized CaMKII in whole lung protein lysates obtained from $MsrA^{-/-}$ and WT asthmatic mice was measured (FIG. 10A). The data show that the levels of oxidized CaMKII correlate with the severity of asthma—being significantly elevated in the lungs of $MsrA^{-/-}$ asthmatic mice. In addition, $MsrA^{-/-}$ mice were sensitized with ovalbumin. $MsrA^{-/-}$ mice show increased airway hyper-reactivity (FIG. 10B) and significantly increased eosinophilic infiltrate (FIG. 10C) compared to controls. These data suggest that CaMKII has an important regulatory role in the asthmatic airway and that the hyper oxidative environment reported in the asthmatic lung may overwhelm the anti-oxidant activity of MsrA and contribute to pathogenesis of asthma.

CONCLUSIONS

The present observations demonstrate that CaMKII is a previously unrecognized downstream nodal signal responsible for activating multiple critical pathways responsible for adverse clinical outcomes in asthma. These observations also contribute important information related to the understanding of ROS and CaMKII in asthma. In the present study, oxidized CaMKII was observed primarily in pulmonary epithelium, while oxidized CaMKII was not consistently observed in pulmonary smooth muscle.

The present data show through study of a genetic mouse lacking p47 (an NADPH oxidase subunit) that NADPH oxidase inhibition (causing reduced oxidation) results in less oxidized CaMKII, reduced airway resistance, and reduced eosinophils in the bronchoalveolar lavage fluid. The data also show that a genetic mouse lacking MsrA results in more oxidized CaMKII, increased airway resistance, and increased eosinophils in the bronchoalveolar lavage fluid.

A mouse that expresses a CaMKII inhibitory peptide (AC3-I) in pulmonary epithelium is resistant to asthma. Further, the data confirm the beneficial effects of inhaled KN-93 in asthma, including reduced airway resistance measurements and reduced eosinophils in bronchoalveolar lavage fluid.

Finally, the alcian blue/PAS stain performed in the foregoing experiments demonstrates that inhibition of CaMKII by both epithelial specific and inhaled small molecule inhibitors of CaMKII can markedly reduce mucus gland metaplasia in murine models. The alcian blue, periodic acid/Schiff (PAS) stain is a well characterized technique to identify a wide range of mucins. As the stain identifies both positive and neutral mucins it affords, greater sensitivity than the periodic acid/Schiff stain alone. Increased mucus gland metaplasia (Aikawa et al. (1992); and Shimura et al. (1996)) and mucus secretions are characteristic findings in asthmatics (Tanizaki et al. (1993)) and are major contributing factors to the severity of asthma exacerbations. During exacerbations mucus overproduction can lead to plugging of the airway lumen (Aikawa et al. (1992); and Shimura et al. (1996)), which limits airflow within the lung. Understanding mechanisms behind mucus gland metaplasia and mucus hyper-secretion is fundamental to improving the day-to-day life of asthmatics.

REFERENCES

1. Chang S, McKinsey T A, Zhang C L, Richardson J A, Hill J A, and Olson E N (2004) Histone deacetylases 5 and 9 govern responsiveness of the heart to a subset of stress signals and play redundant roles in heart development. Mol Cell Biol, 24, 8467-8476.
2. Erickson J R, Joiner M L, Guan X, Kutschke W, Yang J, Oddis C V, Bartlett R K, Lowe J S, O'Donnell S E, ykin-Burns N, Zimmerman M C, Zimmerman K, Ham A J, Weiss R M, Spitz D R, Shea M A, Colbran R J, Mohler P J, and Anderson M E (2008) A dynamic pathway for calcium-independent activation of CaMKII by methionine oxidation. Cell, 133, 462-474.
3. Howe C J, Lahair M M, McCubrey J A, and Franklin R A (2004) Redox regulation of the calcium/calmodulin-dependent protein kinases. J Biol Chem, 279, 44573-44581.
4. Hudmon A and Schulman H (2002) Structure-function of the multifunctional $Ca^{2+}$/calmodulindependent protein kinase II. Biochem J, 364, 593-611.
5. Jain W, Businga T R, Kitagaki K, George C L, O'Shaughnessy P T, and Kline J N (2003) Mucosal immunotherapy with CpG oligodeoxynucleotides reverses a murine model of chronic asthma induced by repeated antigen exposure. Am J Physiol Lung Cell Mol Physiol, 285, L 1137-L 137-L1146.

6. Kirkham P and Rahman I (2006) Oxidative stress in asthma and COPD: antioxidants as a therapeutic strategy. Pharmacol Ther, 111, 476-494.
7. Pang J. Yan C, Natarajan K, Cavet M E, Massett M P, Yin G, and Berk B C (2008) GITI mediates HDAC5 activation by angiotensin II in vascular smooth muscle cells. Arterioscler Thromb Vasc Biol, 28, 892-898.
8. Pfleiderer P J, Lu K K, Crow M T, Keller R S, and Singer H A (2004) Modulation of vascular smooth muscle cell migration by calcium/calmodulin-dependent protein kinase II-delta 2. Am J Physiol Cell Physiol, 286, C1238-C1245.
9. Weiss K B, Sullivan S D, and Lyttle C S (2000) Trends in the cost of illness for asthma in the United States, 1985-1994. J Allergy Clin Immunol, 106, 493-499.
10. Youn H D, Grozinger C M, and Liu J O (2000) Calcium regulates transcriptional repression of myocyte enhancer factor 2 by histone deacetylase 4. J Biol Chem.
11. Horvath I, Donnelly L E, Kiss A, Kharitonov S A, Lim S, Fan Chung K, Barnes P J. Combined use of exhaled hydrogen peroxide and nitric oxide in monitoring asthma, *Am J Respi Crit Care Med*. (1998) 158:1042-1046.
12. Aikawa T, Shimura, S, Sasaki, H, Ebina, M, and Takishima, T. Marked goblet cell hyperplasia with mucus accumulation in the airways of patients who died of severe acute asthma attack. Chest (1992) 101:916-921.
13. Shimura S, Andoh, Y, Haraguchi, M. and Shirato, K. Continuity of airway goblet cells and intraluminal mucus in the airways of patients with bronchial asthma. *Eur Respir J* (1996) 9:1395-1401.
14. Tanizaki Y, Kitani H, Okazaki M, Mifune T, Mitsunobu F, Kimura I. Mucus hypersecretion and eosinophils in bronchoalveolar lavage fluid in adult patients with bronchial asthma. *J Asthma*. (1993) 30(4):257-62.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:
1. A method of treating a pulmonary disease or disorder in a subject comprising administering an effective amount of a compound that modulates Calmodulin Kinase II (CaMKII) activity, thereby treating the pulmonary disease or disorder in the subject.
2. The method of claim 1, wherein the compound inhibits CaMKII activity.
3. The method of claim 1, wherein the pulmonary disease or disorder is asthma.
4. The method of claim 1, wherein the compound is an aryl-indolyl maleimide.
5. The method of claim 4, wherein the compound is an aryl-indolyl maleimide listed in any of Tables 1-14, or an analog or derivative thereof that inhibits CaMKII.
6. The method of claim 1, wherein the compound inhibits the delta isoform of CaMKII.
7. The method of claim 1, wherein the compound is KN-93 or an analog or derivative thereof that inhibits CaMKII.
8. The method of claim 1, wherein the compound is a peptide.
9. The method of claim 1, wherein the compound is administered in a dose of from about 0.05 mg to about 5.0 mg per kilogram of body weight of the subject.
10. The method of claim 1, wherein the compound is administered by inhalation.
11. The method of claim 10, wherein the effective amount is between about 5 and about 500 µg inhaled compound per day.
12. The method of claim 1, wherein the subject is a human.
13. The method of claim 1, wherein the effective amount is at least 1.0 ng/kg of body weight.

* * * * *